(12) United States Patent
Faller et al.

(10) Patent No.: US 12,383,295 B2
(45) Date of Patent: Aug. 12, 2025

(54) ACTUATION MECHANISMS AND LOAD ADJUSTMENT ASSEMBLIES FOR SURGICAL INSTRUMENTS

(71) Applicant: Cilag GmbH International, Zug (CH)

(72) Inventors: Craig N. Faller, Batavia, OH (US); Jacob S. Gee, Cincinnati, OH (US); Paul F. Riestenberg, North Bend, OH (US); Jonathan T. Batross, Cincinnati, OH (US); David A. Monroe, Milford, OH (US); Benjamin D. Dickerson, San Francisco, CA (US); Jeffrey D. Messerly, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 361 days.

(21) Appl. No.: 17/845,391

(22) Filed: Jun. 21, 2022

(65) Prior Publication Data

US 2022/0387067 A1    Dec. 8, 2022

Related U.S. Application Data

(60) Continuation of application No. 16/407,823, filed on May 9, 2019, now Pat. No. 11,413,060, which is a division of application No. 14/448,430, filed on Jul. 31, 2014, now Pat. No. 10,285,724.

(51) Int. Cl.
*A61B 17/32* (2006.01)
*A61B 90/00* (2016.01)
*A61B 17/29* (2006.01)

(52) U.S. Cl.
CPC ...... *A61B 17/320092* (2013.01); *A61B 90/03* (2016.02); *A61B 2017/294* (2013.01); *A61B 2017/320088* (2013.01); *A61B 2017/320094* (2017.08); *A61B 2017/320095* (2017.08)

(58) Field of Classification Search
CPC ... A61B 2017/294; A61B 17/29; A61B 17/32; A61B 17/320092; A61B 17/320068; A61B 90/00; A61B 90/03
See application file for complete search history.

(56) References Cited

U.S. PATENT DOCUMENTS

| | | |
|---|---|---|
| 6,214,023 B1 | 4/2001 | Whipple et al. |
| 6,480,796 B2 | 11/2002 | Wiener |
| 6,537,291 B2 | 3/2003 | Friedman et al. |
| 6,662,127 B2 | 12/2003 | Wiener et al. |

(Continued)

FOREIGN PATENT DOCUMENTS

| | | |
|---|---|---|
| EP | 1946708 B1 | 6/2011 |
| JP | 2004129871 A | 4/2004 |

*Primary Examiner* — Vi X Nguyen

(57) ABSTRACT

An ultrasonic surgical instrument includes an inner tube, an outer tube, an ultrasonic blade, and a clamp member pivotably moveable relative to the ultrasonic blade. The ultrasonic blade is acoustically coupled to an ultrasonic transducer. The clamp member pivotably movable relative to the ultrasonic blade between an open configuration and an approximated configuration with respect to the ultrasonic blade, wherein the clamp member is pivotably coupled to the inner tube, wherein the clamp member is pivotably coupled to the outer tube, and wherein movement of the outer tube relative to the inner tube between the first position and the second position transitions the clamp member between the open configuration and the approximate configuration.

9 Claims, 34 Drawing Sheets

(56) References Cited

U.S. PATENT DOCUMENTS

| | | |
|---|---|---|
| 6,790,216 B1 | 9/2004 | Ishikawa |
| 6,977,495 B2 | 12/2005 | Donofrio |
| 7,077,853 B2 | 7/2006 | Kramer et al. |
| 7,179,271 B2 | 2/2007 | Friedman et al. |
| 7,273,483 B2 | 9/2007 | Wiener et al. |
| 8,142,461 B2 | 3/2012 | Houser et al. |
| 8,623,027 B2 | 1/2014 | Price et al. |
| 8,663,220 B2 | 3/2014 | Wiener et al. |
| 9,192,428 B2 | 11/2015 | Houser et al. |
| 9,352,173 B2 | 5/2016 | Yamada et al. |
| 10,285,724 B2 | 5/2019 | Faller et al. |
| 11,413,060 B2 | 8/2022 | Faller et al. |
| 2004/0097911 A1 | 5/2004 | Murakami et al. |
| 2006/0079879 A1* | 4/2006 | Faller ............ A61B 17/320092 606/40 |
| 2006/0224160 A1 | 10/2006 | Trieu et al. |
| 2008/0234708 A1* | 9/2008 | Houser .......... A61B 17/320068 606/169 |
| 2009/0105750 A1 | 4/2009 | Price et al. |
| 2009/0270853 A1 | 10/2009 | Yachi et al. |
| 2012/0022583 A1 | 1/2012 | Sugalski et al. |
| 2014/0005702 A1 | 1/2014 | Timm et al. |
| 2014/0135804 A1 | 5/2014 | Weisenburgh, II et al. |

\* cited by examiner

ACTUATION MECHANISMS AND LOAD ADJUSTMENT ASSEMBLIES FOR SURGICAL INSTRUMENTS

CROSS-REFERENCE TO RELATED APPLICATIONS

This application is a continuation application claiming priority under 35 U.S.C. § 120 to U.S. patent application Ser. No. 16/407,823, entitled ACTUATION MECHANISMS AND LOAD ADJUSTMENT ASSEMBLIES FOR SURGICAL INSTRUMENTS, filed May 9, 2019, now U.S. Patent Application Publication No. 2019/0262030, which is a divisional application claiming priority under 35 U.S.C. § 121 to U.S. patent application Ser. No. 14/448,430, entitled ACTUATION MECHANISMS AND LOAD ADJUSTMENT ASSEMBLIES FOR SURGICAL INSTRUMENTS, filed Jul. 31, 2014, which issued on May 14, 2019 as U.S. Pat. No. 10,285,724, the entire disclosures of which are hereby incorporated by reference herein.

BACKGROUND

The present disclosure is related generally to surgical instruments including ultrasonic instruments. Ultrasonic surgical instruments, such as ultrasonic scalpels, are used in many applications in surgical procedures by virtue of their unique performance characteristics. Ultrasonic surgical instruments can be configured for open surgical use, laparoscopic, or endoscopic surgical procedures including robotic-assisted procedures.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Furthermore, it will be appreciated that for conciseness and clarity, spatial terms such as "vertical," "horizontal," "up," and "down", for example, may be used herein with respect to the illustrated embodiments. However, these terms are used to assist the reader and are not intended to be limiting and absolute.

Figure 1:
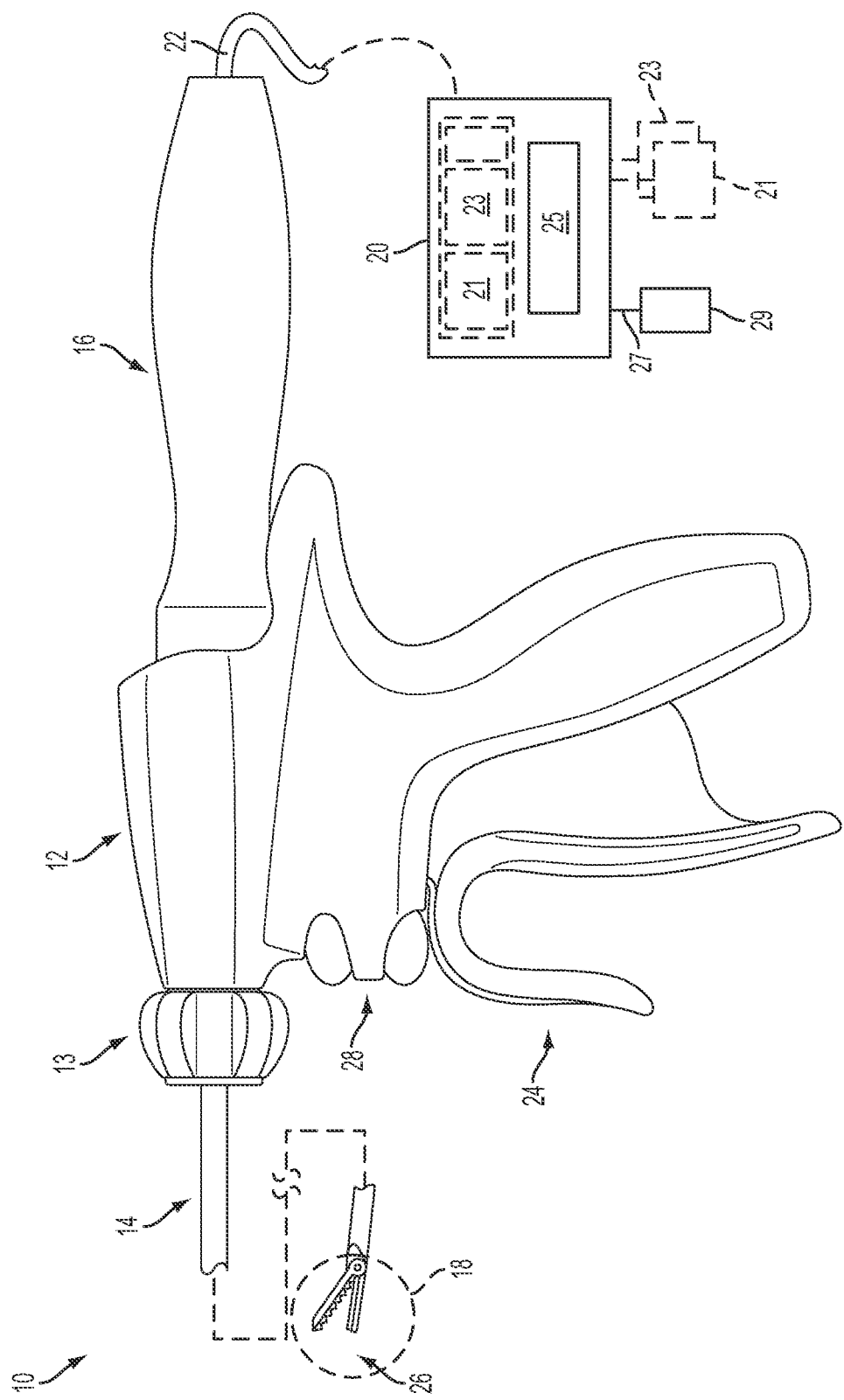
FIG. 1 illustrates a surgical system including a surgical instrument and an ultrasonic generator.

Turning now to the figures, FIG. 1 illustrates a right side view of one embodiment of an ultrasonic surgical instrument 10. In the illustrated embodiment, the ultrasonic surgical instrument 10 may be employed in various surgical procedures including endoscopic or traditional open surgical procedures. In one example embodiment, the ultrasonic surgical instrument 10 comprises a handle assembly 12, an elongated shaft assembly 14, an ultrasonic transducer 16, and a blade 66. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 can be mechanically engaged to the elongated shaft assembly 14 and portions of the end effector assembly 26. The ultrasonic transducer 16 can be electrically coupled to a generator 20 via a cable 22. In certain instances, the generator can be integrated with the handle assembly 12, for example. Although the majority of the drawings depict a multiple end effector assembly 26 for use in connection with laparoscopic surgical procedures, the ultrasonic surgical instrument 10 may be employed in more traditional open surgical procedures and in other embodiments, may be configured for use in endoscopic procedures. For the purposes herein, the ultrasonic surgical instrument 10 is described in terms of an endoscopic instrument; however, it is contemplated that an open and/or laparoscopic version of the ultrasonic surgical instrument 10 also may include the same or similar operating components and features as described herein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In the example embodiment illustrated in FIG. 1, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a subtherapeutic RF signal to implement a tissue impedance measurement module. In one embodiment, the electrosurgical/RF generator module 23 comprises a bipolar radio frequency generator as described in more detail below. In one embodiment, the electrosurgical/RF generator module 12 may be configured to monitor electrical impedance Z, of tissue T and to control the characteristics of time and power level based on the tissue T by way of a return electrode provided on a clamp member of the end effector assembly 26. Accordingly, the electrosurgical/RF generator module 23 may be configured for subtherapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instrument," the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S.

patents, all of which are incorporated by reference herein in their entireties: U.S. Pat. No. 6,480,796 (METHOD FOR IMPROVING THE START UP OF AN ULTRASONIC SYSTEM UNDER ZERO LOAD CONDITIONS); U.S. Pat. No. 6,537,291 (METHOD FOR DETECTING BLADE BREAKAGE USING RATE AND/OR IMPEDANCE INFORMATION); U.S. Pat. No. 6,662,127 (METHOD FOR DETECTING PRESENCE OF A BLADE IN AN ULTRASONIC SYSTEM); U.S. Pat. No. 6,977,495 (DETECTION CIRCUITRY FOR SURGICAL HANDPIECE SYSTEM); U.S. Pat. No. 7,077,853 (METHOD FOR CALCULATING TRANSDUCER CAPACITANCE TO DETERMINE TRANSDUCER TEMPERATURE); U.S. Pat. No. 7,179,271 (METHOD FOR DRIVING AN ULTRASONIC SYSTEM TO IMPROVE ACQUISITION OF BLADE RESONANCE FREQUENCY AT STARTUP); and U.S. Pat. No. 7,273,483 (APPARATUS AND METHOD FOR ALERTING GENERATOR FUNCTION IN AN ULTRASONIC SURGICAL SYSTEM). Furthermore, U.S. Patent Application Publication No. 2014/0005702, entitled ULTRASONIC SURGICAL INSTRUMENTS WITH DISTALLY POSITIONED TRANSDUCERS, and filed on Jun. 29, 2012, is incorporated by reference herein in its entirety.

It will be appreciated that in various embodiments, the generator 20 may be configured to operate in several modes. In one mode, the generator 20 may be configured such that the ultrasonic generator module 21 and the electrosurgical/RF generator module 23 may be operated independently.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the sub-therapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the sub-therapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while an ultrasonic blade such as, for example, the blade 66 of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade 66 of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a pre-selected constant level in order to achieve substantially constant excursion at the end effector 18 of the acoustic assembly. In yet another embodiment, a third feedback loop in the control system 25 monitors impedance between electrodes located in the end effector assembly 26.

In ultrasonic operation mode, the electrical signal supplied to the acoustic assembly may cause the distal end of the end effector 18, to vibrate longitudinally in the range of, for example, approximately 20 kHz to 250 kHz. According to various embodiments, the blade 66 may vibrate in the range of about 54 kHz to 56 kHz, for example, at about 55.5 kHz. In other embodiments, the blade 66 may vibrate at other frequencies including, for example, about 31 kHz or about 80 kHz. The excursion of the vibrations at the blade 66 can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

In various instances, when the acoustic assembly is energized, a vibratory motion standing wave is generated through the acoustic assembly. The amplitude of the vibratory motion at any point along the acoustic assembly depends on the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node.

Figure 2:
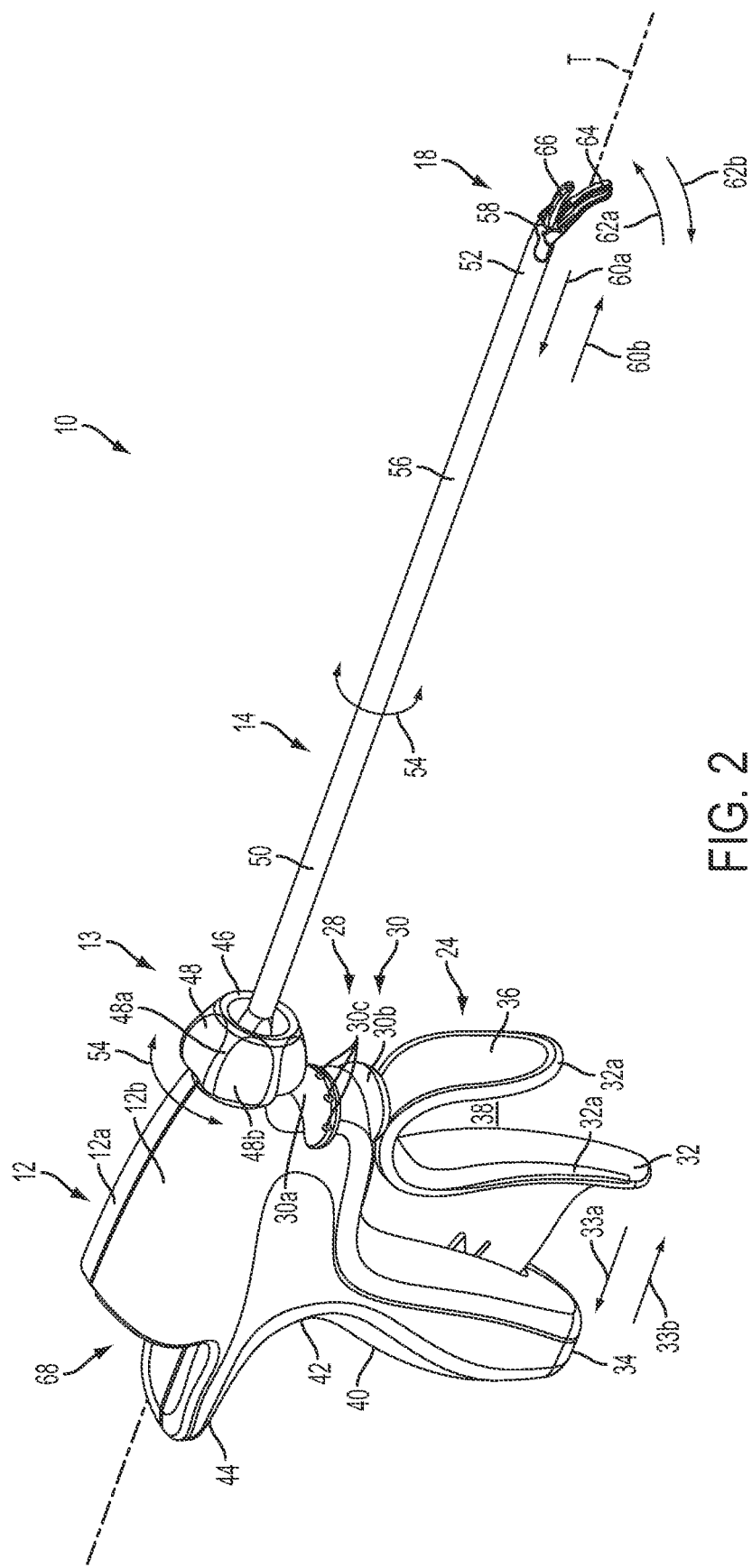
FIG. 2 illustrates the surgical instrument shown in FIG. 1.

FIG. 2 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element may cause the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33B. In one example embodiment, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30a and a second projecting knob 30b to set the power setting of the ultrasonic transducer 16 between a minimum power level (e.g., MIN) and a maximum power level (e.g., MAX). In another embodiment, the rocker switch may pivot between a standard setting and a special setting. The special setting may allow one or more special programs to be implemented by the device. The toggle switch 30 rotates about the central pivot as the first projecting knob 30a and the second projecting knob 30b are actuated. The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30a comprises a plurality of tactile elements 30c, e.g., textured projections or "bumps" in the illustrated embodiment, to allow the user to differentiate the first projecting knob 30a from the second projecting knob 30b. It will be appreciated by those skilled in the art that several ergonomic features may be incorporated into the handle assembly 12. Such ergonomic features are described in U.S. Patent Application Publication No. 2009/0105750 entitled ERGONOMIC SURGICAL INSTRUMENTS, now U.S. Pat. No. 8,623,027, which is incorporated by reference herein in its entirety.

In one example embodiment, the toggle switch 30 may be operated by the hand of the user. The user may easily access the first and second projecting knobs 30a, 30b at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another embodiment, the rocker switch may pivot the instrument 10 between a standard setting and a special setting. The special setting may allow one or more special programs to be implemented by the instrument 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46a that is exposed at the distal end. The end cap portion 46a of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12a and a second portion 12b. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

Figure 2A:
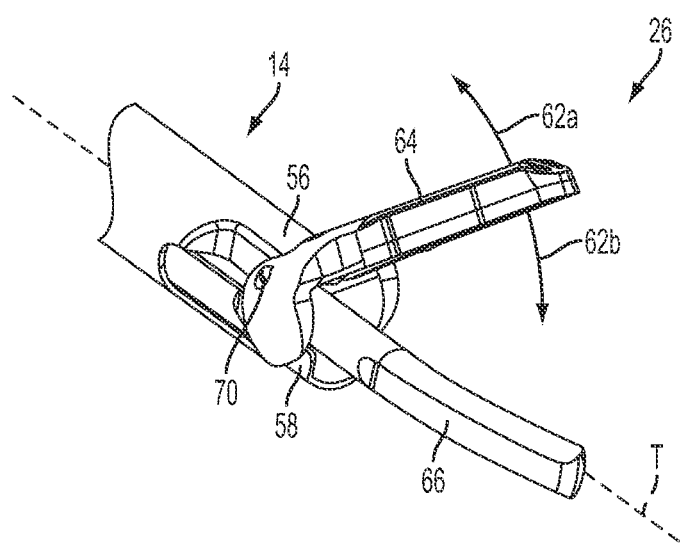
FIG. 2A illustrates a distal portion of the surgical instrument of FIG. 2 including an ultrasonic end effector.

Referring to FIGS. 1-2A, the elongated shaft assembly 14 comprises a proximal end 50 adapted to mechanically engage the handle assembly 12 and the distal rotation assembly 13, and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp member 64, which is pivotable about a pivot point 70, to open and close the clamp member 64 in response to the actuation and/or release of the trigger 32. For example, in the illustrated embodiment, the clamp member 64 is movable in direction 62A from an open position to a closed position about a pivot point 70 when the trigger 32 is squeezed in direction 33A. The clamp member 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp member 58 and a blade 66. The jaws of the clamping mechanism of the end effector assembly 26 are formed by clamp member 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp member 64. Squeezing the trigger 32 in direction 33A moves the clamp member 64 in direction 62A from an open position, wherein the clamp member 64 and the blade 66 are disposed in a spaced relation relative to one another, to a clamped or closed position, wherein the clamp member 64 and the blade 66 cooperate to grasp tissue therebetween. The clamp member 64 may comprise a clamp pad to engage tissue between the blade 66 and the clamp member 64. Releasing the trigger 32 in direction 33B moves the clamp member 64 in direction 62B from a closed relationship, to an open position, wherein the clamp member 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

Figure 3:
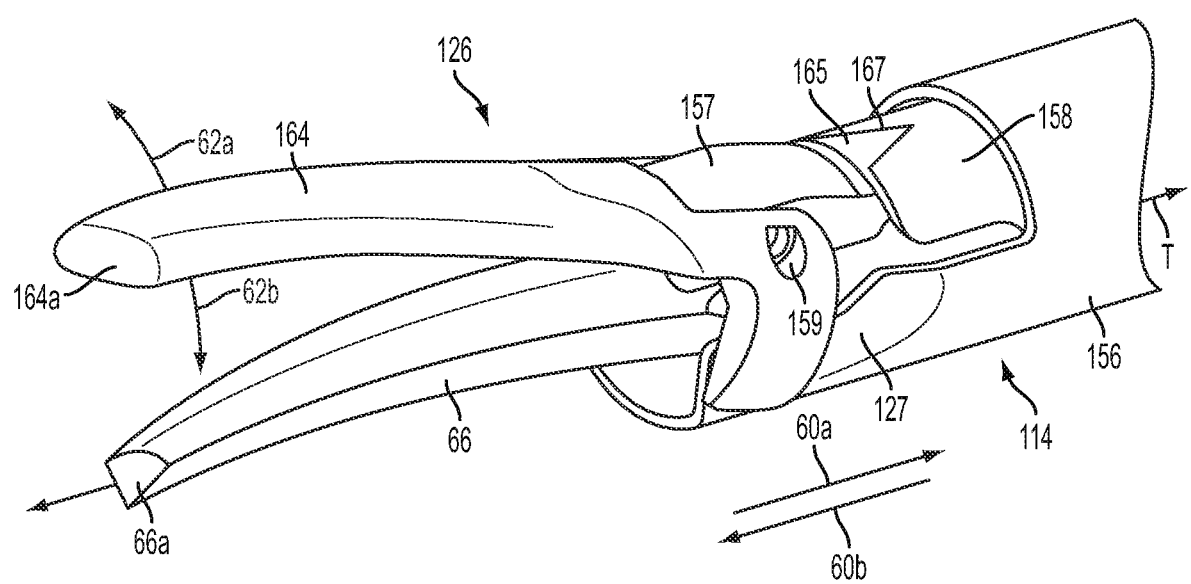
FIG. 3 illustrates a distal portion of the surgical instrument of FIG. 2 including an ultrasonic end effector.
Figure 4:
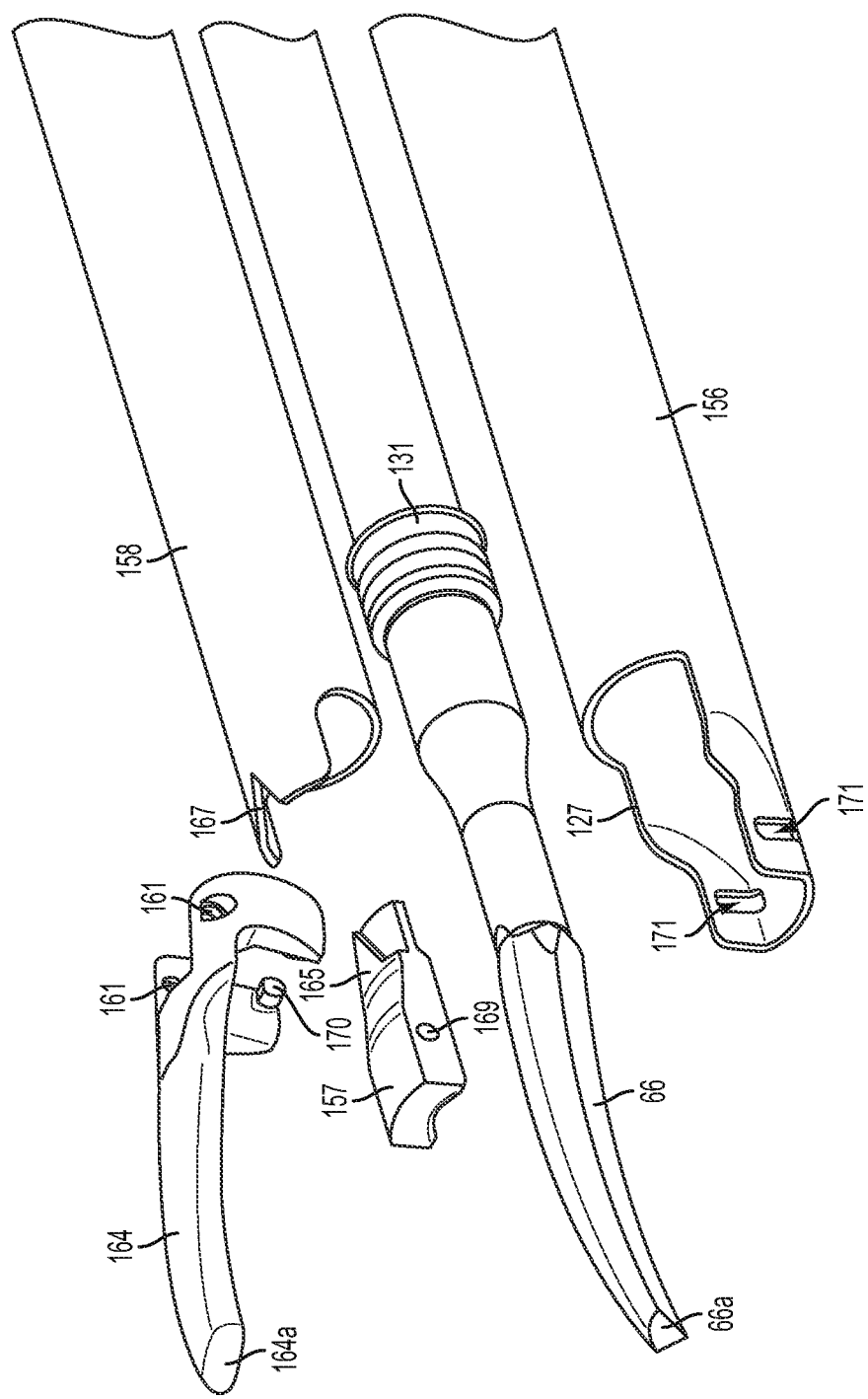
FIG. 4 illustrates an exploded view of the distal portion of FIG. 3.
Figure 5:
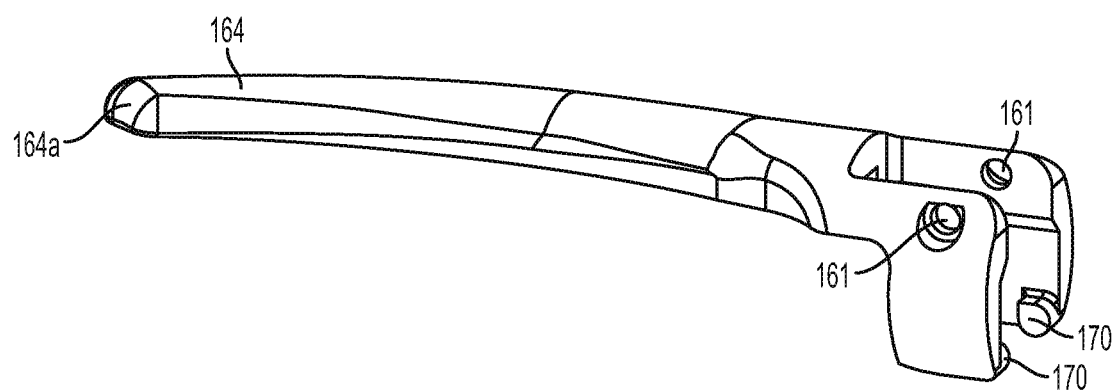
FIG. 5 illustrates a clamp member of the surgical instrument of FIG. 2.

Referring now to FIGS. 3-5, in certain instances, the surgical instrument 10 may include an elongated shaft assembly 114, which is similar in many respects to the elongated shaft assembly 14. In addition, as illustrated in FIG. 3, the surgical instrument 10 may include an end effector assembly 126, which is similar in many respects to the end effector assembly 26, for example. In certain instances, the end effector assembly 126 may include a clamp member 164, for example. In certain instances, the elongated shaft assembly 114 may include an outer tubular reciprocating member 156 and an inner tubular member 158, for example. In certain instances, the outer tubular reciprocating member 156 and the inner tubular member 158 may extend coaxially along the longitudinal axis "T", for example. In certain instances, the inner tubular member 158 may be partially surrounded by the outer tubular reciprocating member 156, for example. In certain instances, the blade 66 may extend through the inner tubular member 158; the inner tubular member 158 can be configured to receive the blade 66.

In certain instances, the blade 66 can be cooperatively coupled to the inner tubular member 158, for example. In certain instances, a sealing member 131 (FIG. 4) can be disposed between the blade 66 and inner tubular member 158, and may resist fluid entry into the elongated shaft assembly 114, for example. In certain instances, the sealing member 131 can be disposed around, or at least partially around, the blade 66, for example. In certain instances, the sealing member 131 may be positioned at or adjacent to a distal node of vibration. In certain instances, the sealing member 131 may be positioned at or adjacent to a node closest to the distal end of the blade 66, for example. In various instances, the sealing member 131 may comprise a sealing lip or a ring disposed around the blade 66, for example.

In certain instances, the outer tubular reciprocating member 156 can be axially movable relative to the inner tubular member 158. For example, the outer tubular reciprocating member 156 can be retracted proximally and/or advanced distally relative to the inner tubular member 158. In certain instances, the ultrasonic blade 66 can be coupled to the inner tubular member 158. In such instances, the outer tubular reciprocating member 156 can be retracted proximally and/or advanced distally relative to the blade 66 and the inner tubular member 158, for example.

A proximal portion of the outer tubular reciprocating member 156 can be operably coupled to the trigger 32 of the handle assembly 12 to move in either direction 160A or 160B in response to the actuation and/or release of the trigger 32. A distal portion 127 of the outer tubular reciprocating member 156 can be movably coupled to the end effector assembly 126. In at least one example, the distal portion 127 of the outer tubular reciprocating member 156 can be pivotably coupled to the clamp member 164. Reciprocating the outer tubular reciprocating member 156 between a first or retracted position and a second or advanced position may cause the clamp member 164 to be transitioned between an approximated configuration and an open configuration with the ultrasonic blade 66, for example. FIG. 3, for example, illustrates the clamp member 164 in a partially open configuration with respect to the blade 66.

In certain instances, the clamp member 164 may be pivotably coupled to the outer tubular reciprocating member 156 at a pivot point defined by pivot pins 170 (FIG. 5) which can be received in designated slots 171 (FIG. 4) on the distal portion 127 of the outer tubular reciprocating member 156, for example. In such instances, the clamp member 164 can be pivoted about the pins 170, in response to the reciprocating motion of the outer tubular reciprocating member 156, to transition between the approximated configuration and the open configuration with respect to the blade 66.

Further to the above, the clamp member 164 can also be pivotably coupled to the inner tubular member 158, and can be configured to pivot relative to the inner tubular member 158 in response to the reciprocating motion of the outer tubular reciprocating member 156, for example. In certain instances, the inner tubular member 158 may comprise a connection member 157 disposed at a distal end portion of the inner tubular member 158, as illustrated in FIG. 3. In certain instances, the clamp member 164 can be pivotably coupled to the connection member 157. For example, a pivot pin 159 may extend through openings 161 of the clamp member 164 and through the connection member 157 to pivotably couple the clamp member 164 to the connection member 157.

In any event, reciprocating the outer tubular reciprocating member 156 between the first position and the second position may cause the clamp member 164 to pivot about the pin 159 and the pins 170 to transition between the open configuration and the approximated configuration with respect to the blade 66, for example. In certain instances, the pin 159, which couples the clamp member 164 to the connection member 157, and the pins 170, which couple the clamp member 164 to the distal portion 127 of the outer tubular reciprocating member 156, may reside on opposite sides of the blade 66, as illustrated in FIG. 3. In other words, the blade 66 can be disposed between the distal portion 127 and the blade 66.

In certain instances, as illustrated in FIG. 3, the blade 66 may extend between the distal portion 127 of the outer tubular reciprocating member 156 and the connection member 157. The distal portion 127 may be partially open which may expose, or partially expose, the connection member 157, for example. In certain instances, the side of the connection member 157 may comprise a shape that complements the blade 66, for example.

In certain instances, the connection member 157 can be manufactured with the inner tubular member 158 as a single unit. For example, the connection member 157 and the inner tubular member 158 can be injection molded together as a single unit. In other instances, the connection member 157 and the inner tubular member 158 can be manufactured separately and attached together during assembly of the surgical instrument 10. In at least one example, the connection member 157 and the inner tubular member 158 may comprise complimentary portions 165 and 167, respectively, which can be welded together, for example, to attach the connection member 157 to the inner tubular member 158. Other mechanisms for manufacturing and/or attaching the inner tubular member 158 and the connection member 157 are contemplated by the present disclosure. The reader will appreciate that manufacturing of the connection member 157 separately may ensure a greater accuracy in the dimensions of the connection member 157, which may lead to a better alignment between the clamp member 164 and the blade 66 during assembly of the surgical instrument 10.

In certain instances, as illustrated in FIG. 4, the connection member 157 may comprise a greater thickness than the wall of the inner tubular member 158. The increased thickness of the connection member 157 may provide stability to the clamp member 164 during the transition between the open configuration and the approximated configuration. In addition, the increased thickness of the connection member 157 may provide sufficient space for a through-hole 169 for receiving the pin 159, for example.

Further to the above, the present disclosure provides a method for assembling a surgical instrument such as, for example, the surgical instrument 10. In certain instances, the method for assembling the surgical instrument 10 may ensure proper alignment between the blade 66 and the clamp member 164. The reader will appreciate that it can be desirable to accurately align the clamp member 164 with the blade 66 to ensure proper transmission of ultrasonic energy through the blade 66 to tissue captured between the clamp member 164 and the blade 66 in the approximated configuration. In certain instances, it can be desirable for the clamp member 164 to be rotationally aligned with the blade 66, for example, to ensure that a curvature of the clamp member 164 is aligned with a curvature of the blade 66, for example. In certain instances, it can be desirable for a distal end 66a of the blade 66 to be axially aligned with a distal end 164a of the clamp member 164, for example.

In any event, the method for assembling the surgical instrument 10 may comprise the steps of: positioning the blade 66 with respect to the inner tubular member 158, positioning the inner tubular member 158 with respect to the outer tubular reciprocating member 156, coupling the clamp member 164 to the outer tubular reciprocating member 156, coupling the clamp member 164 to the connection member 157, and/or attaching the connection member 157 to the inner tubular member 158, for example. The reader will appreciate that reserving the attachment of the connection member 157 to the inner tubular member 158 until the assembly stage can facilitate fine adjustment of the relative positions of the clamp member 164 and the connection member 157 thereby ensuring the proper rotational and axial alignment between the blade 66 and the clamp member 164.

Figure 6:
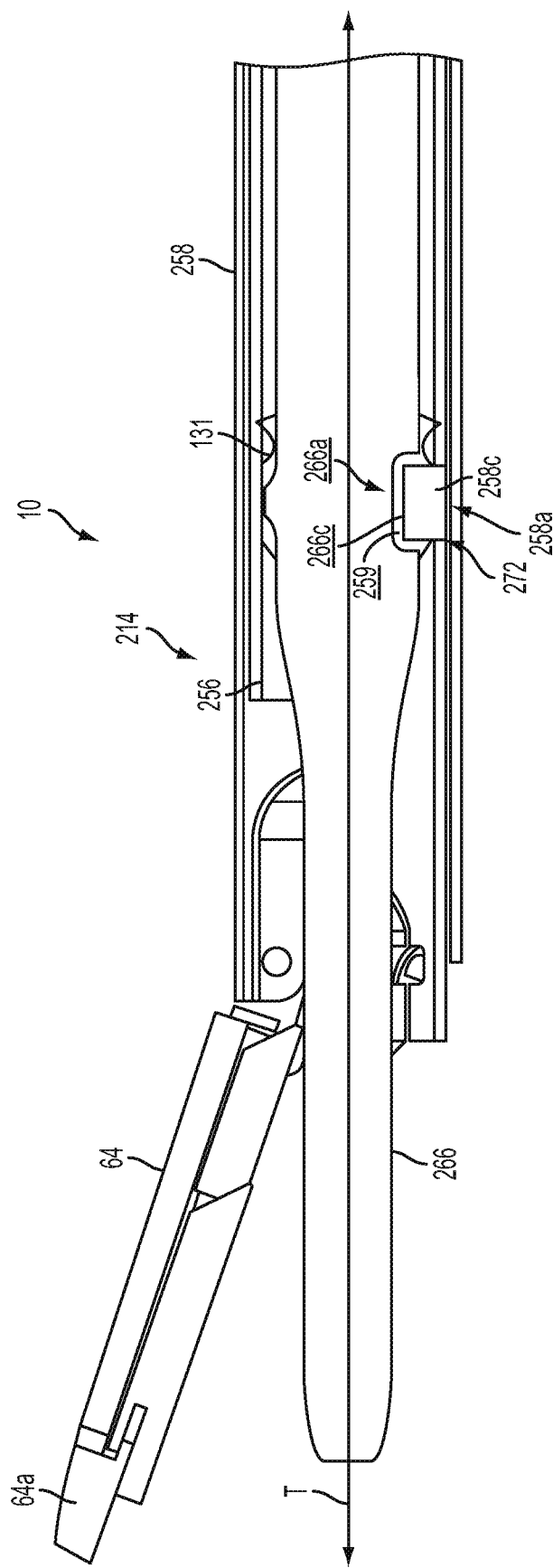
FIG. 6 illustrates a longitudinal cross-sectional view of the distal portion of FIG. 2A.

Referring now to FIGS. 6-9, the surgical instrument 10 may include an elongated shaft assembly 214. FIG. 6 illustrates a partial cross-sectional view of the elongated shaft assembly 214. The elongated shaft assembly 214 is similar in many respects to the elongated shaft assembly 14 and/or the elongated shaft assembly 114. In certain instances, the elongated shaft assembly 214 can be adapted for coupling engagement with the end effector assembly 26 to actuate the clamp member 64 in a similar manner to the elongated shaft assembly 14, for example. In certain instances, the elongated shaft assembly 214 can be adapted for coupling engagement with the end effector assembly 126 to actuate the clamp member 164 in a similar manner to the elongated shaft assembly 114, for example.

In any event, the elongated shaft assembly 214 may include an outer tube 256, which is similar in many respects to the outer tubular member 56 and/or the outer tubular member 156, for example. In addition, the elongated shaft assembly 214 may include an inner tube 258, which is similar in many respects to the inner tubular member 58 and/or the inner tubular member 158, for example. Furthermore, the elongated shaft assembly 214 may include an ultrasonic blade 266, which is similar in many respects to the ultrasonic blade 66. For example, like the ultrasonic blade 66, the ultrasonic blade 266 can be acoustically coupled to the transducer 16.

Figure 6A:
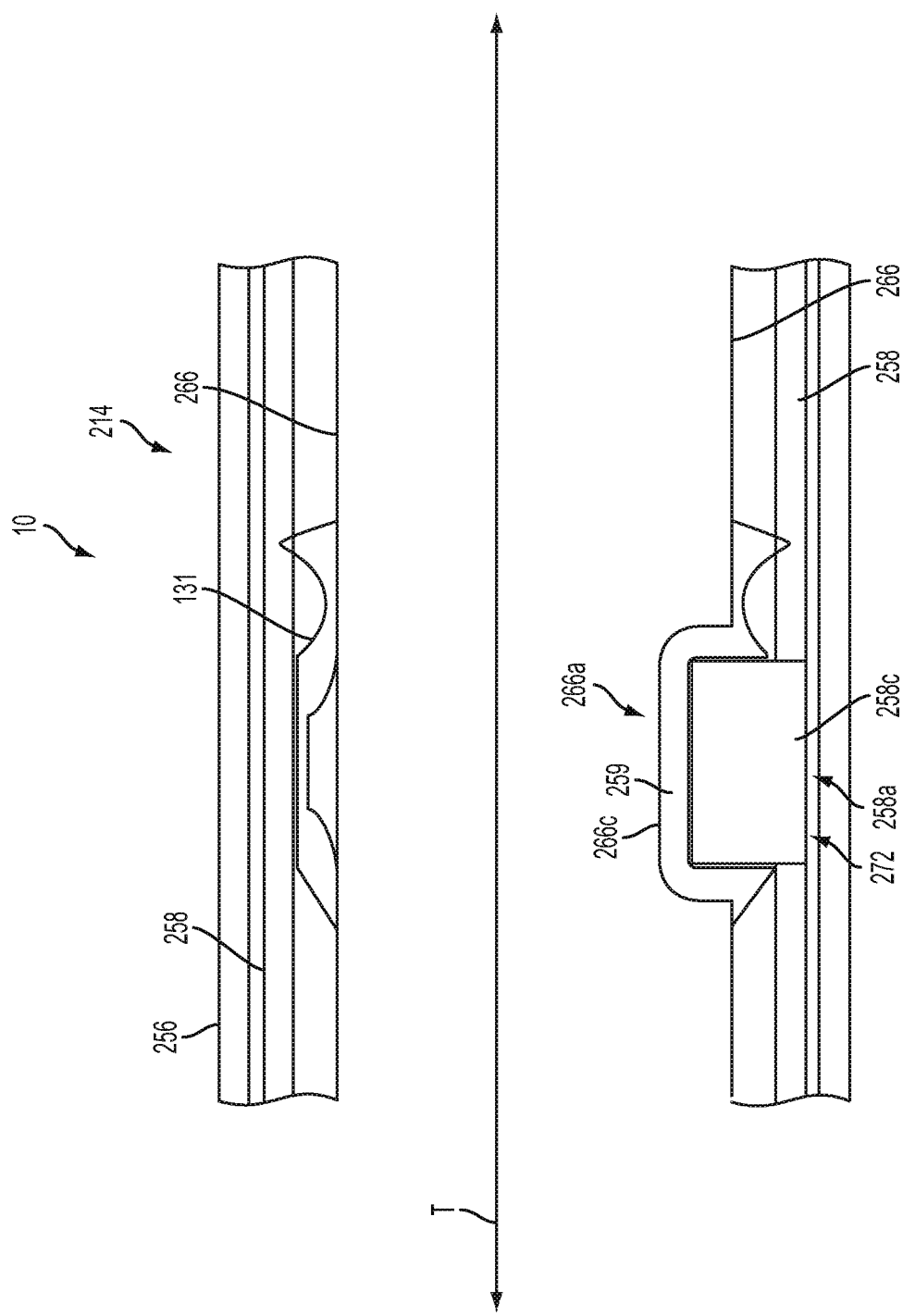
FIG. 6A illustrates a partial longitudinal cross-sectional view of an elongated shaft assembly of the surgical instrument of FIG. 2.

In various instances, in an exemplary assembled form of the surgical instrument 10, the outer tube 256 and the inner tube 258 may extend coaxially along a longitudinal axis "T", as illustrated in FIG. 6A. In certain instances, the inner tube 258 may be partially surrounded by the outer tube 256, for example. In certain instances, the blade 266 may extend through the inner tube 258; the inner tube 258 can be configured to receive the blade 266. In certain instances, the blade 266 can be cooperatively coupled to the inner tube 258, for example.

As described above, rotational and/or axial positioning and/or alignment of an ultrasonic blade such as, for example, the ultrasonic blade 266 with respect to other components of the surgical instrument 10 can be important in ensuring proper performance of the surgical instrument 10 including but not limited to efficient transmission of the ultrasonic energy. In various instances, the inner tube 258 and/or the blade 266 may include one or more alignment features, which may establish the rotational and/or axial positioning and/or alignment of the blade 266 with respect to other components of the surgical instrument 10 and maintain such rotational and/or axial positioning and/or alignment during use of the surgical instrument 10 in a surgical procedure, for example. In at least one example, as illustrated in FIG. 6, the inner tube 258 may comprise an alignment feature 258*a*, and the blade 266 may comprise an alignment feature 266*a*.

Figure 8:
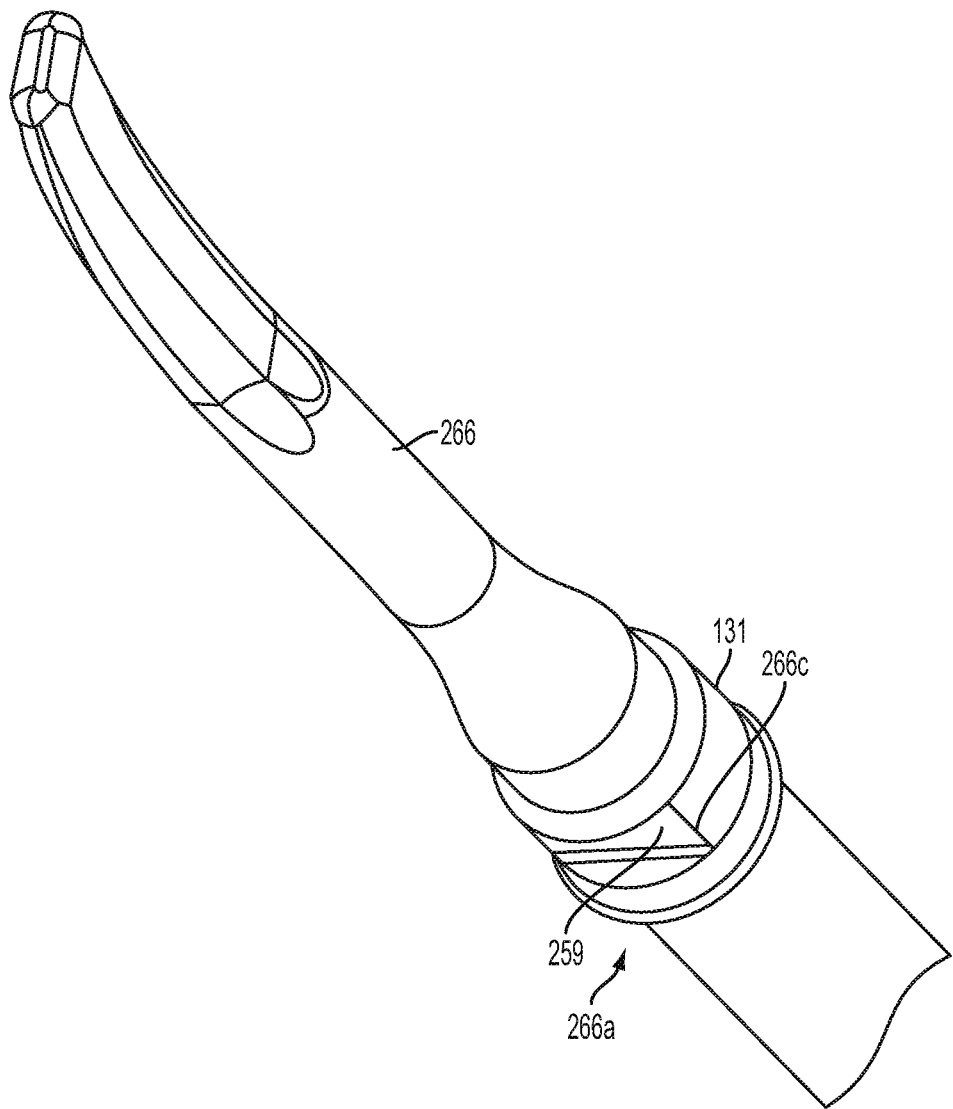
FIG. 8 illustrates a partial perspective view of an ultrasonic blade of the surgical instrument of FIG. 2.
Figure 9:
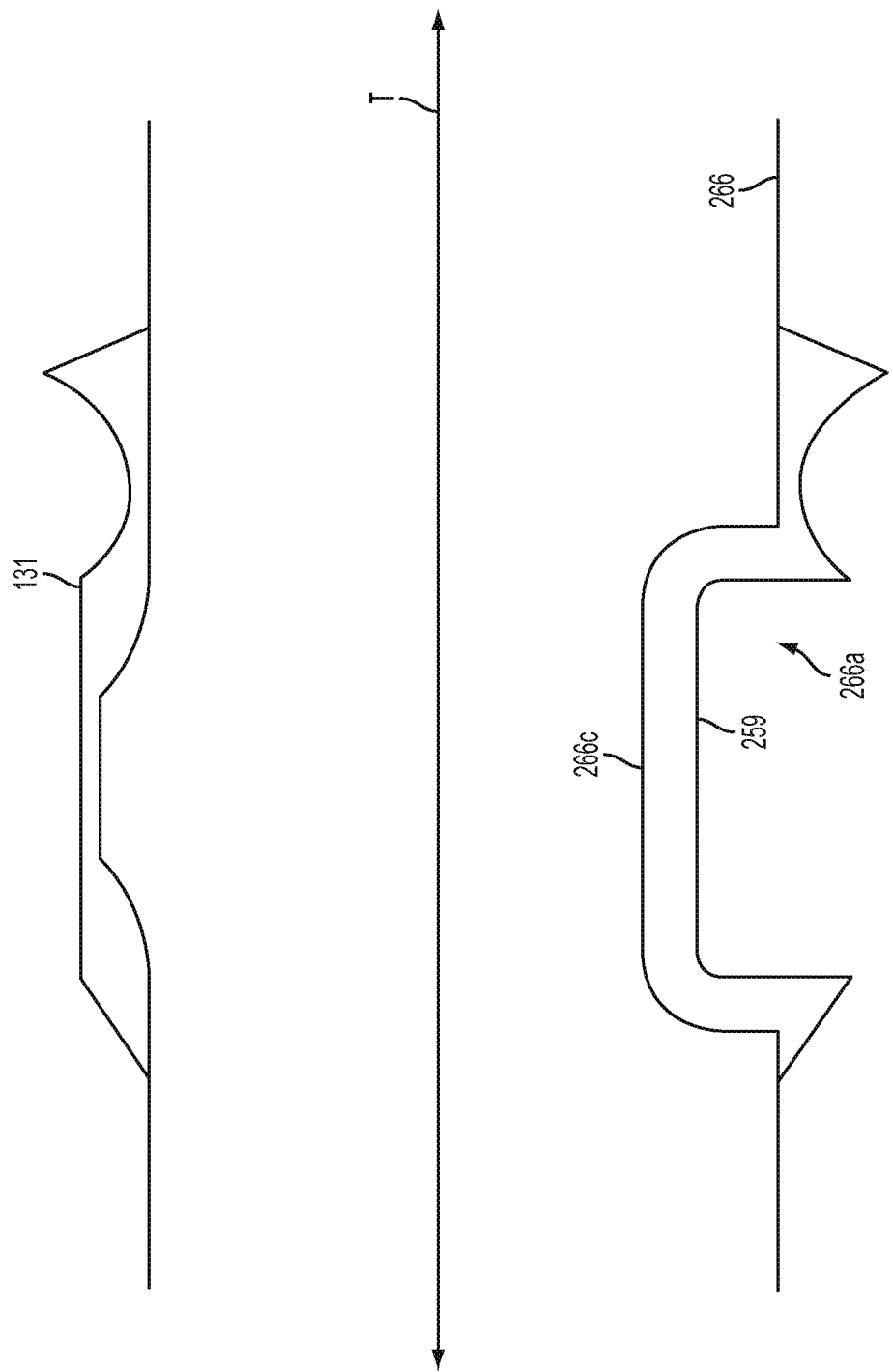
FIG. 9 illustrates a partial longitudinal cross-sectional view of the ultrasonic blade of FIG. 7.

In various instances, referring primarily to FIGS. 6 and 8, the alignment features 258*a* and/or 266*a* may be positioned at a node of vibration along the blade 266. As described above, a minimum or zero crossing in the vibratory motion may exist at a node of vibration; positioning the alignment features 258*a* and/or 266*a* at the node of vibration may reduce interference with the operation of the blade 266, which may increase the efficiency of the ultrasonic energy transmission, for example. In certain instances, the alignment features 258*a* and/or 266*a* may be positioned at a distal node of vibration. In certain instances, the alignment features 258*a* and/or 266*a* may be positioned at a node closest to the distal end of the blade 266, for example.

In various instances, referring to FIGS. 6-9, the alignment feature 258*a* and/or the alignment feature 266*a* may comprise one or more vibration isolating portions 259 such as, for example, an overmolded silicone rubber bushing. In various instances, the vibration isolating portions 259 can be overmolded onto the blade 266 and/or the inner tube 258, for example. In certain instances, the vibration isolating portions 259 can be integrated with the sealing member 131, as illustrated in FIG. 6.

Figure 10:
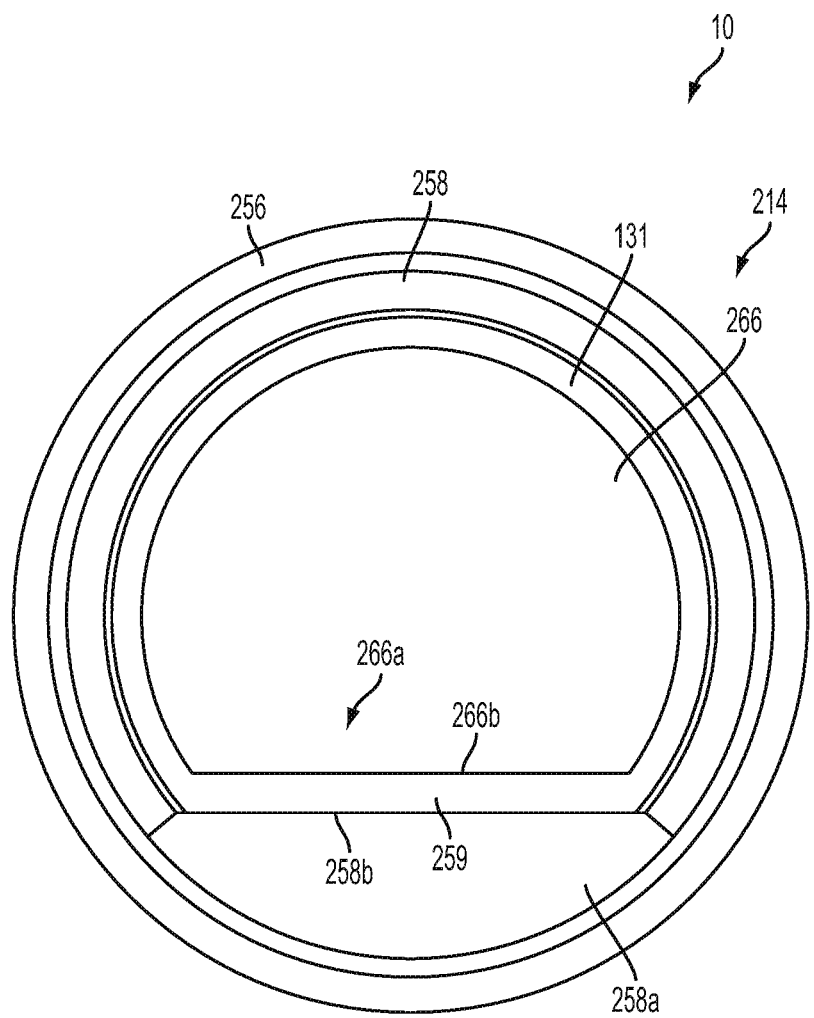
FIG. 10 illustrates a transverse cross-sectional view of an elongated shaft assembly of the surgical instrument of FIG. 2.

In certain instances, as illustrated in FIG. 6A, the alignment feature 266*a* of the blade 266 may comprise a receiving portion 266*c*, which can be adapted to receive a constraining member 258*c* of the alignment feature 258*a* of the inner tube 258, for example. In certain instances, the receiving portion 266*c* can be interfaced with the constraining member 258*c* to establish rotational and/or axial positioning and/or alignment of the blade 266 with respect to other components of the surgical instrument 10 and maintain such rotational and/or axial positioning and/or alignment during use of the surgical instrument 10 in a surgical procedure, for example. As illustrated in FIG. 6A, the receiving portion 266*c* may be comprised of a slot, a notch, a groove, an aperture, and/or a gap in the body of the blade 266, which can be adapted for mating engagement with the constraining member 258*c*, for example. For example, the constraining member 258*c* may comprise a tab, a tongue or a latch, which can be inserted into a socket of the receiving portion 266*c* to establish rotational and/or axial positioning and/or alignment of the blade 266 with respect to other components of the surgical instrument 10 and maintain such rotational and/or axial positioning and/or alignment during use of the surgical instrument 10 in a surgical procedure, for example. In certain instances, as illustrated in FIG. 10, the alignment feature 258*a* may comprise a flat section 258*b* which can be aligned with a corresponding flat section 266*b* of the blade 266 to establish rotational alignment between the blade 266 and the inner tube 258 and maintain such alignment during use of the surgical instrument 10 in a surgical procedure, for example.

Figure 7:
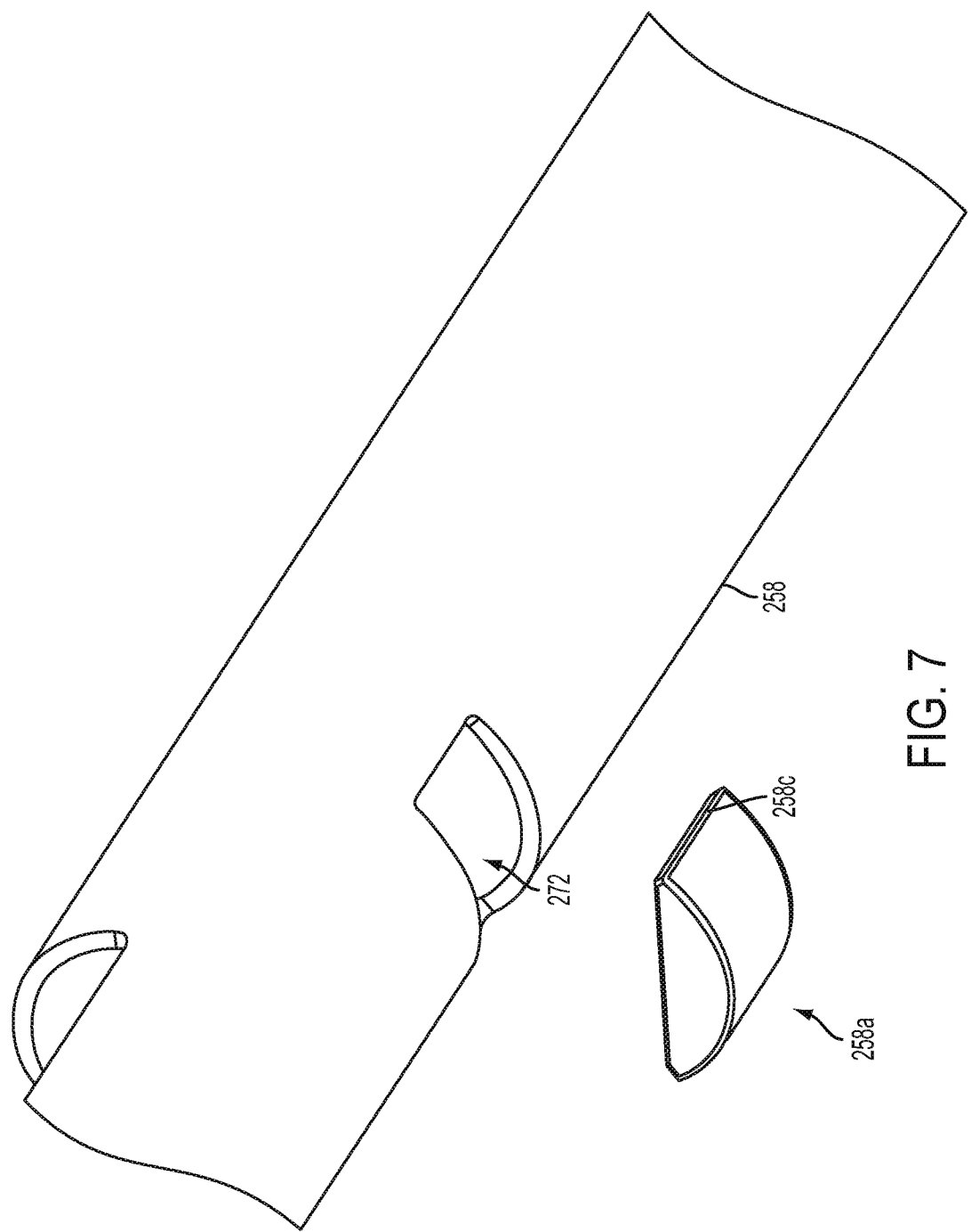
FIG. 7 illustrates a partial perspective view of an inner tube and an alignment feature of the surgical instrument of FIG. 2.

Referring to FIG. 7, in certain instances, the inner tube 258 may comprise a side opening 272 in a wall of the inner tube 258, for example. In certain instances, the constraining member 258*c* can be interfaced with the receiving portion 266*c* by inserting at least a portion of the constraining member 258*c* through the side opening 272 of the inner tube 258 into engagement with the receiving portion 266*c*, for example. In certain instances, the blade 266 can be inserted into the inner tube 258 and aligned therewith such that the receiving portion 266*c* is faced with the side opening 272 of the inner tube. The constraining member 258*c* can then be inserted, or at least partially inserted, through the side opening 272 of the inner tube 258 and into engagement with the receiving portion 266*c*, which may establish and maintain rotational and/or axial positioning and/or alignment between the blade 266 with the inner tube 258, for example. In certain instances, the constraining member 258*c* may be fixedly attached to the inner tube 258 at the side opening 272, for example. In certain instances, the constraining member 258*c* can be welded to the wall of the inner tube 258 at the side opening 272, for example. In certain instances, the constraining member 258*c* can be assembled with the inner tube 258 through a snap-like interface, locking tabs, and/or an adhesive, for example. In at least one example, the constraining member 258*c* may comprise a c-clip or a pin which can be welded to the inner tube 258, for example.

Figure 11:
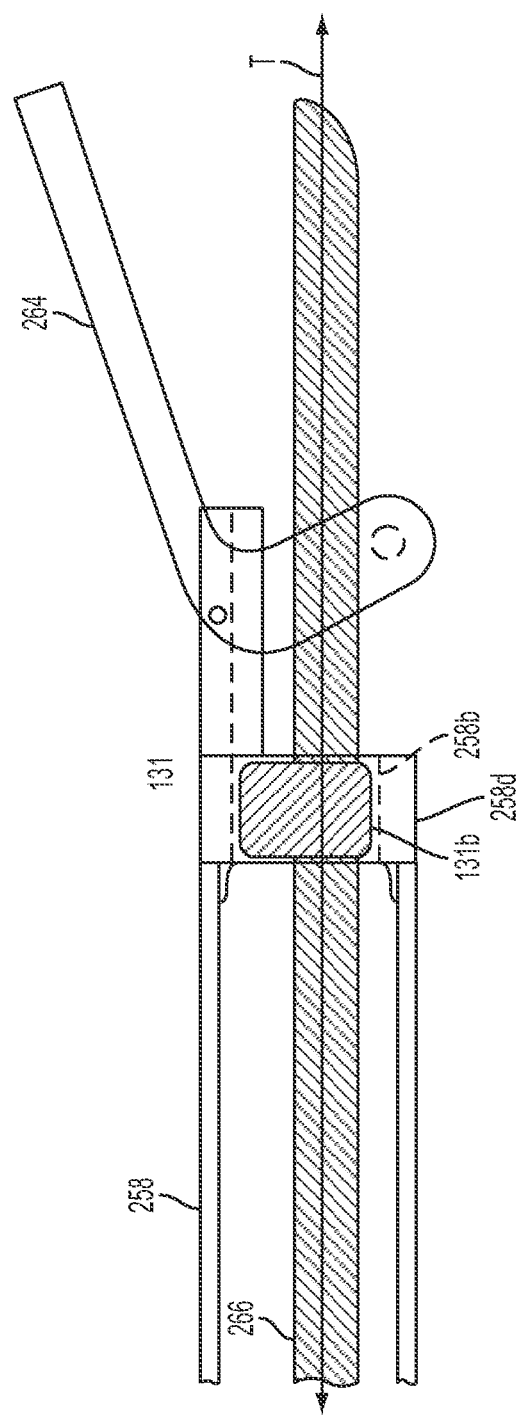
FIG. 11 illustrates a cross-sectional view of a distal portion of the surgical instrument of FIG. 2 with a removed outer tube.
Figure 12:
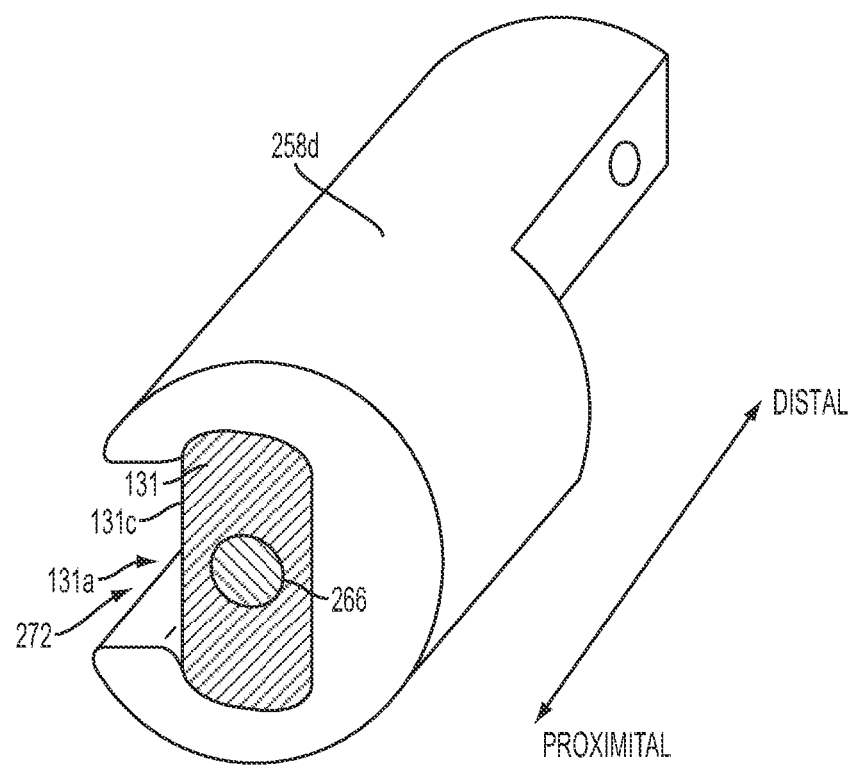
FIG. 12 illustrates a perspective cross-sectional view of a retaining cap of the distal portion of FIG. 11.

Referring mainly to FIGS. 11 and 12, in certain instances, the sealing member 131 may comprise an alignment feature 131*a*, which is similar in many respects to the alignment feature 266*a* of the blade 266. For example, the alignment feature 131*a* can be employed in a similar manner to the alignment feature 266*a* in establishing and maintaining the rotational and/or axial positioning and/or alignment of the blade 266 with respect to other components of the surgical instrument 10. In certain instances, the alignment feature 131*a* may comprise a receiving portion 131*c* similar to the receiving portion 266*c*, which can be adapted to receive constraining member 258*c*. In certain instances, the alignment feature 131*a* may comprise a flat section 131*b* that is similar in many respects to the flat section 266*b* of the alignment feature 266*a*. In certain instances, the flat section 131*b* can be adapted for interfacing with the flat section 258*b* of the inner tube 258, as illustrated in FIG. 12.

In certain instances, as illustrated in FIGS. 11 and 12, the alignment feature 258*a* of the inner tube 258 can be positioned at a distal portion of the inner tube 258. In certain instances, the inner tube 258 may comprise a retaining cap 258d at a distal portion of the inner tube 258. In certain instances, the alignment feature 258a may be positioned at an inner wall of the retaining cap 258d, for example. In certain instances, as illustrated in FIG. 12, the retaining cap 258d may comprise the side opening 272, for example. A constraining member such as, for example, the constraining member 258c can be interfaced with the receiving portion 131c by inserting at least a portion of the constraining member 258c through the side opening 272 of the retaining cap 258d to engage the receiving portion 131c, for example.

In various instances, the sealing member 131 can be coupled to the blade 266. For example, the sealing member 131 can be snuggly fitted around, or at least partially around, the blade 266, as illustrated in FIG. 12. In such instances, interfacing the alignment feature 131a of the sealing member 131 with the alignment feature 258a of the retaining cap 258d may establish and maintain rotational and/or axial positioning and/or alignment between the sealing member 131 and the retaining cap 258d, which in turn may establish and maintain the rotational and/or axial positioning and/or alignment between the blade 266 and the inner tube 258, for example.

Figure 13:
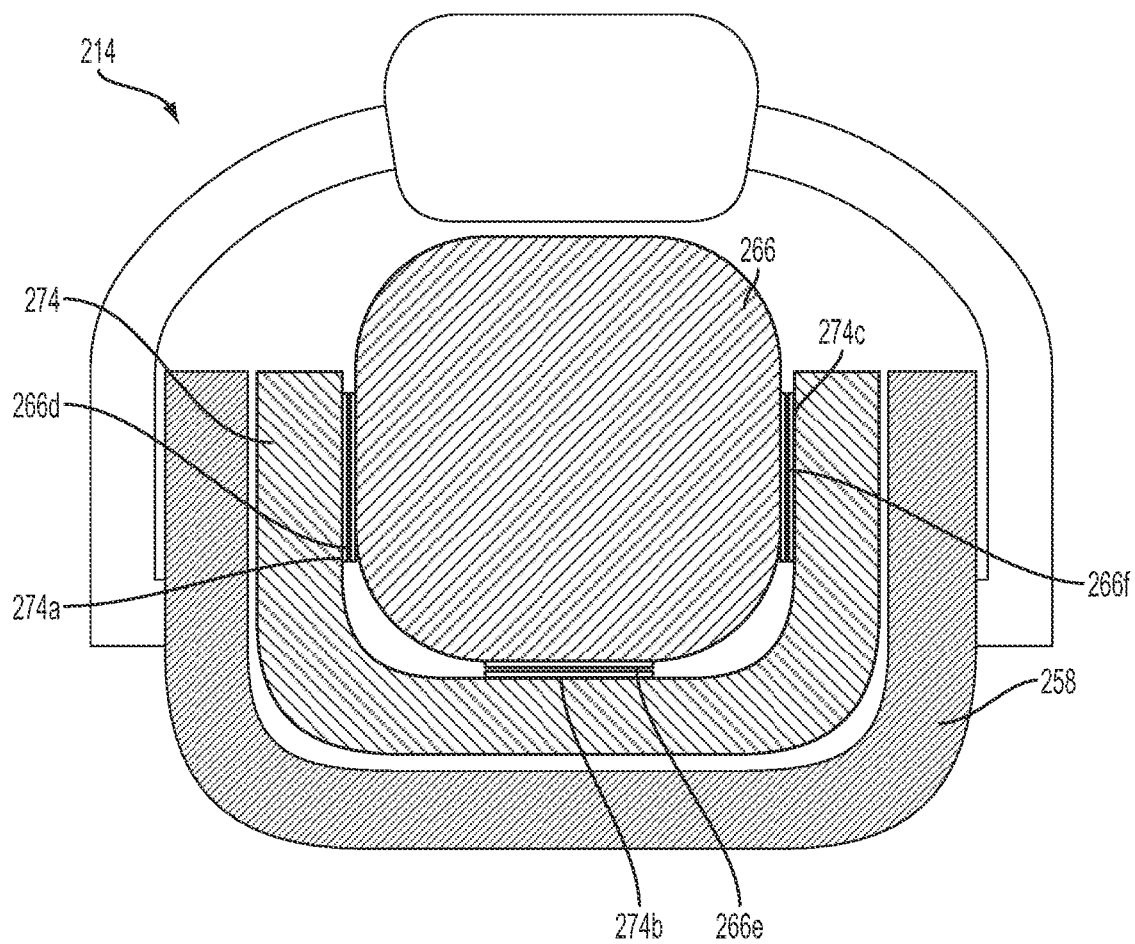
FIG. 13 illustrates a transverse cross-sectional view of an ultrasonic blade, an inner tube, and an insert of the surgical instrument of FIG. 2.

In various instances, referring primarily to FIG. 13, the elongated shaft assembly 214 may comprise an insert 274, which can be positioned between the inner tube 258 and the blade 266. In certain instances, the insert 274 may comprise a plurality of flat sections 274a-274c, which can be adapted to interface with a plurality of corresponding flat sections 266d-266f on the blade 266, as illustrated in FIG. 13. Such an arrangement may establish and maintain rotational positioning and/or alignment between the insert 274 and the blade 266, which in turn may establish and maintain the rotational positioning and/or alignment between the blade 266 and the inner tube 258, for example.

In certain instances, the insert 274 can be fixedly attached to the inner tube 258. In at least one example, the insert 274 can be welded to the inner tube 258. In such instances, the insert 274 can be positioned in place between the blade 266 and the inner tube 258 during assembly of the surgical instrument 10. Once the rotational positioning and/or alignment between the insert 274 and the blade 266 is adjusted to a desired degree, the insert 274 can be welded to the inner tube 258 to maintain such rotational positioning and/or alignment, for example.

In certain instances, the insert 274 can be positioned at or adjacent to a distal node of vibration. In certain instances, the insert 274 may be positioned at a node closest to the distal end of the blade 266, for example. In at least one example, the insert 274 may comprise a single flat wall insertable between the blade 266 and the inner tube 258. In at least one example, the insert 274 may comprise two flat walls insertable between the blade 266 and the inner tube 258. The flat walls may intersect at a perpendicular, or at least substantially perpendicular, angle and. In at least one example, as illustrated in FIG. 13, the insert 274 may comprise three flat walls insertable between the blade 266 and the inner tube 258.

Figure 14:
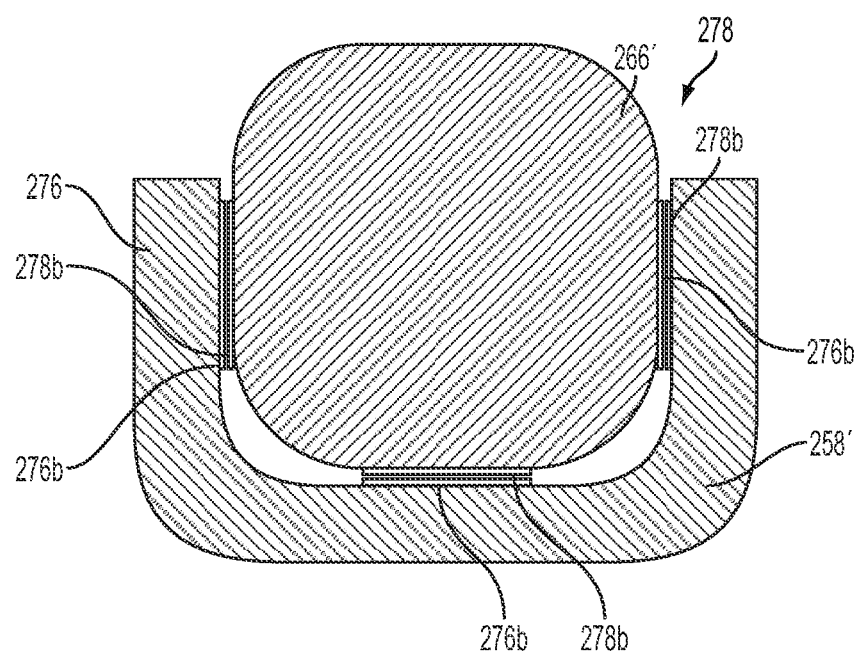
FIG. 14 illustrates a transverse cross-sectional view of an ultrasonic blade and a channel of the surgical instrument of FIG. 2.
Figure 15:
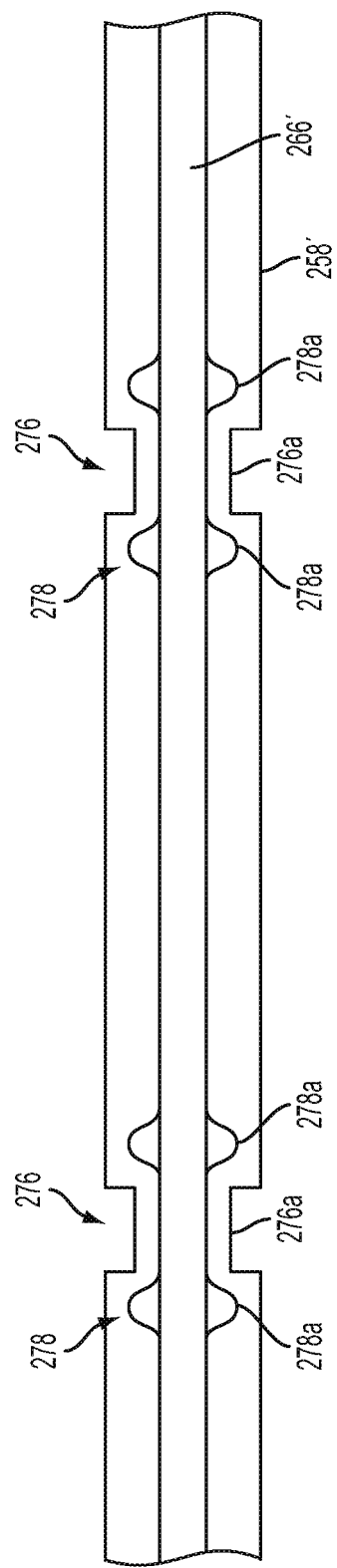
FIG. 15 illustrates a partial longitudinal cross-sectional view of the ultrasonic blade and the channel of FIG. 14.

In various instances, referring primarily to FIG. 14, the elongated shaft assembly 214 can be modified by replacing the inner tube 258 with a channel 258' which, in certain instances, may comprise a semi-circular transverse cross-section, for example. In various instances, a blade 266', which is similar in many respects to the blade 266, can be assembled with the channel 258'. As illustrated in FIG. 15, the channel 258' and the blade 266' may comprise complimenting alignment features 276 and 278, respectively. In various instances, the alignment features 276 and 278 can be similar in many respects to the alignment features 258a and 266a, for example. In certain instances, the alignment features 276 and 278 can be interfaced to establish and maintain rotational and/or axial positioning and/or alignment between the channel 258' and the blade 266', for example.

In certain instances, as illustrated in FIG. 15, the alignment feature 276 of the channel 258' may comprise one or more divots 276a. In certain instances, each divot 276a can be received between two divots 278a of the alignment feature 278 of the blade 266', for example. The divots 276a and 278a can cooperate to establish and maintain rotational and/or axial positioning and/or alignment between the channel 258' and the blade 266', for example, and maintain such to establish and maintain rotational and/or axial positioning and/or alignment during use of the surgical instrument 10 in a surgical procedure.

In certain instances, the alignment features 276 and 278 may comprise complimenting flat sections which can be interfaced to establish and maintain rotational positioning and/or alignment between the channel 258' and the blade 266', for example. In at least one example, the alignment feature 276 may comprise three flat sections 276b which can be disposed on three inner walls of the channel 258', as illustrated in FIG. 14. In addition, the blade 266' may comprise three flat sections 278b for mating engagement with the flat sections 276b, for example. In various instances, the alignment features 276 and/or 278 can be positioned at or adjacent to one or more nodes of vibration. In certain instances, the alignment features 276 and/or 278 may be positioned at one or more nodes of vibration at a distal portion of the blade 266, for example.

In various instances, as illustrated in FIG. 6, the elongated shaft assembly 214 can be adapted for coupling engagement with the end effector assembly 26 to actuate the clamp member 64 between an open configuration and an approximated configuration to capture tissue between the clamp member 64 and the blade 266, for example. In such instances, the clamp member 64 can be actuated to generate a clamping force against the blade 266. In various instances, the elongated shaft assembly 214 can be adapted for coupling engagement with the end effector assembly 126 to actuate the clamp member 164 between an open configuration and an approximated configuration to capture tissue between the clamp member 164 and the blade 266, for example. In such instances, the clamp member 164 can be actuated to generate a clamping force against the blade 266.

In certain instances, the clamping force generated by the clamp member 164 or the clamp member 64 can be applied along a vector which intersects a plane P defined by the flat section 266b of the blade 266, for example. In certain instances, the vector of the generated clamping force may form a perpendicular, or at least substantially perpendicular, angle with the plane P, for example. In certain instances, the angle between the vector of the generated clamping force and the plane P defined by the flat section 266b of the blade 266 can be any value selected from a range of about 85 degrees to about 95 degrees. In certain instances, the angle between the vector of the generated clamping force and the plane P defined by the flat section 266b of the blade 266 can be any value selected from a range of about 89 degrees to about 91 degrees. In certain instances, the angle between the vector of the generated clamping force and the plane P defined by the flat section 266b of the blade 266 can be about 90 degrees.

In various instances, as illustrated in FIG. 6, the clamp member 64 of the end effector assembly 26 can be moved between the open configuration and the closed configuration along, or at least substantially along, a plane P1 intersecting the plane P defined by the flat section 266b of the blade 266. In certain instances, the plane P1 can be perpendicular, or at least substantially perpendicular, with the plane P. In certain instances, the angle between the plane P1 and the plane P is any angle selected from a range of about 85 degrees to about 95 degrees. In certain instances, the angle between the plane P1 and the plane P is any angle selected from a range of about 89 degrees to about 91 degrees.

Similarly, the clamp member 164 of the end effector assembly 126 can be moved between the open configuration and the closed configuration along, or at least substantially along, a plane P2 intersecting the plane P defined by the flat section 266b of the blade 266. In certain instances, the plane P2 can be perpendicular, or at least substantially perpendicular, with the plane P. In certain instances, the angle between the plane P2 and the plane P is any angle selected from a range of about 85 degrees to about 95 degrees. In certain instances, the angle between the plane P2 and the plane P is any angle selected from a range of about 89 degrees to about 91 degrees.

In various instances, as illustrated in FIG. 6, the clamp member 64 of the end effector assembly 26 and the flat section 258b of the inner tube 258 can be disposed on opposite sides of the plane P defined by the flat section 266b of the blade 266. In such instances, the clamping force generated by the clamp member 64 may bias, motivate, and/or move the alignment feature 266a of the blade 266 toward the alignment feature 258a of the inner tube 258. In certain instances, the clamping force generated by the clamp member 64 may bring the alignment feature 266a of the blade 266 into contact with the alignment feature 258a of the inner tube 258.

Similarly, the clamp member 164 of the end effector assembly 126 and the flat section 258b of the inner tube 258 can be disposed on opposite sides of the plane P defined by the flat section 266b of the blade 266. In such instances, the clamping force generated by the clamp member 164 may bias, motivate, and/or move the alignment feature 266a of the blade 266 toward the alignment feature 258a of the inner tube 258. In certain instances, the clamping force generated by the clamp member 164 may bring the alignment feature 266a of the blade 266 into contact with the alignment feature 258a of the inner tube 258.

Referring now to FIGS. 16-20, an ultrasonic surgical instrument 310 is depicted. The surgical instrument 310 is similar in many respects to the surgical instrument 10. For example, the instrument 310 includes an ultrasonic blade 366, which is similar in many respects to the ultrasonic blade 66. Like the blade 66, the blade 366 can be acoustically coupled to the ultrasonic transducer 16, for example. Furthermore, the instrument 310 may include a clamp member 364, which is similar in many respects to the clamp member 64 and/or the clamp member 164, for example.

In various instances, the surgical instrument 310 can be employed in open surgery. In certain instances, the clamp member 364 can be transitioned between an approximated configuration and an open configuration with respect to the ultrasonic blade 366 by actuating a handle 301, for example. In certain instances, the clamp member 364 may be pivotably coupled to a support shaft 358 at a pivot point 370. In such instances, the clamp member 364 can be pivoted about the point 370 by actuating the handle 301. The blade 366 may extend through the support shaft 358; the support shaft 358 can be configured to receive the blade 266.

In various instances, rotational and/or axial positioning and/or alignment of an ultrasonic blade such as, for example, the ultrasonic blade 366 with respect to other components of the surgical instrument 310 can be important in ensuring proper performance of the surgical instrument 310 including but not limited to efficient transmission of the ultrasonic energy. In various instances, the support shaft 358 and/or the blade 366 may include one or more alignment features, which may establish the rotational and/or axial positioning and/or alignment of the blade 366 with respect to other components of the surgical instrument 310. The alignment features can also maintain the rotational and/or axial positioning and/or alignment during use of the surgical instrument 310 in a surgical procedure, for example. In at least one example, as illustrated in FIG. 17, the support shaft 358 may comprise an alignment feature 358a, and the blade 366 may comprise an alignment feature 366a.

Figure 16:
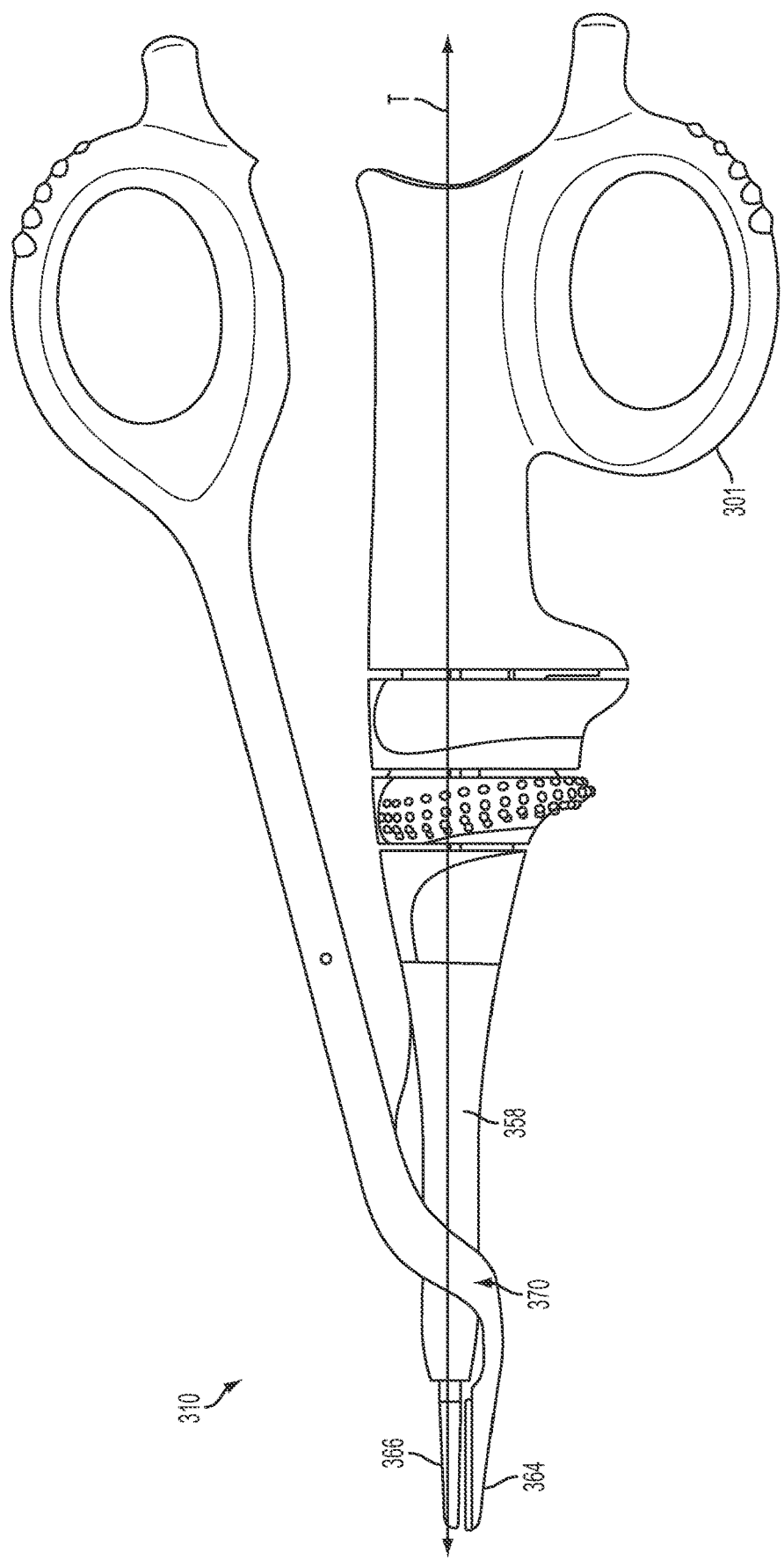
FIG. 16 illustrates a side elevational view of a surgical instrument.
Figure 17:
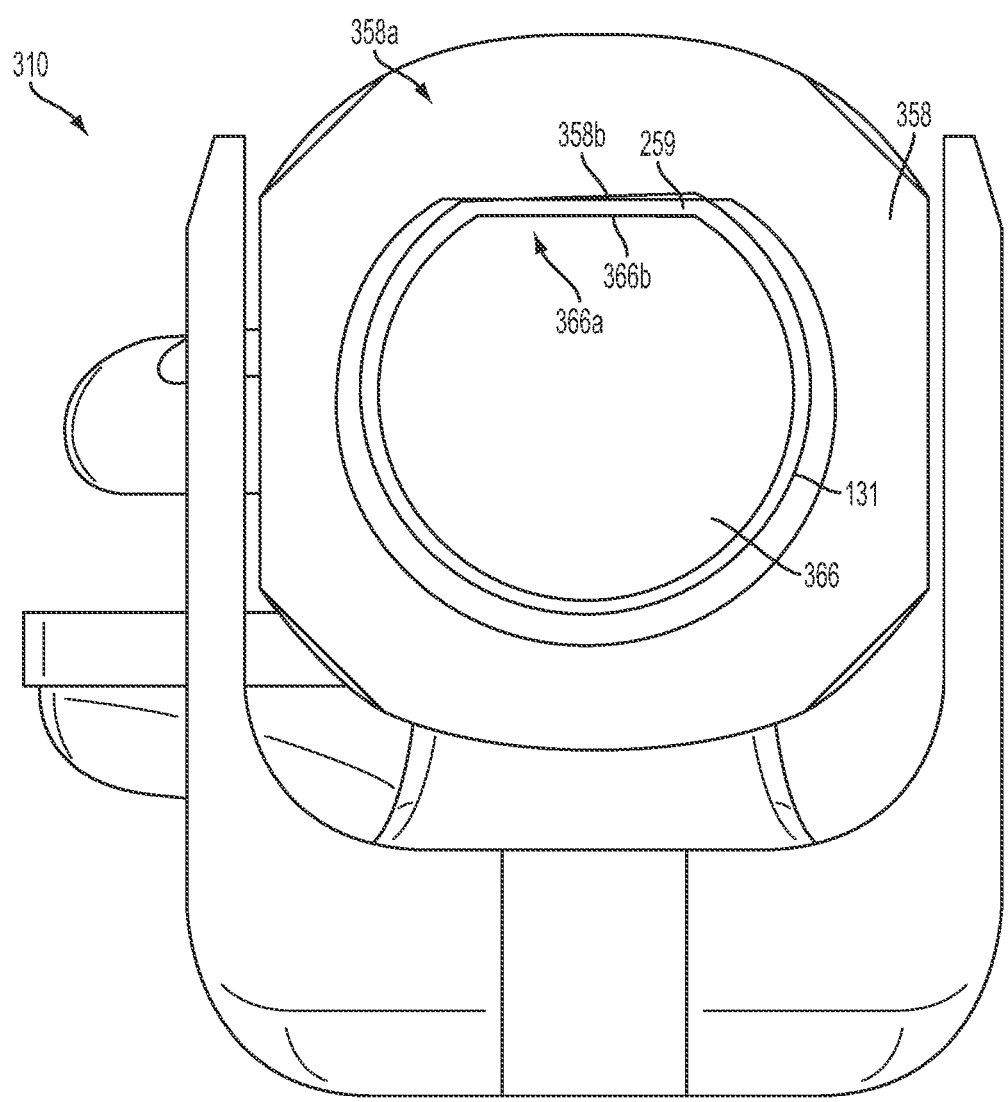
FIG. 17 illustrates a transverse cross-sectional view of the surgical instrument of FIG. 16.
Figure 18:
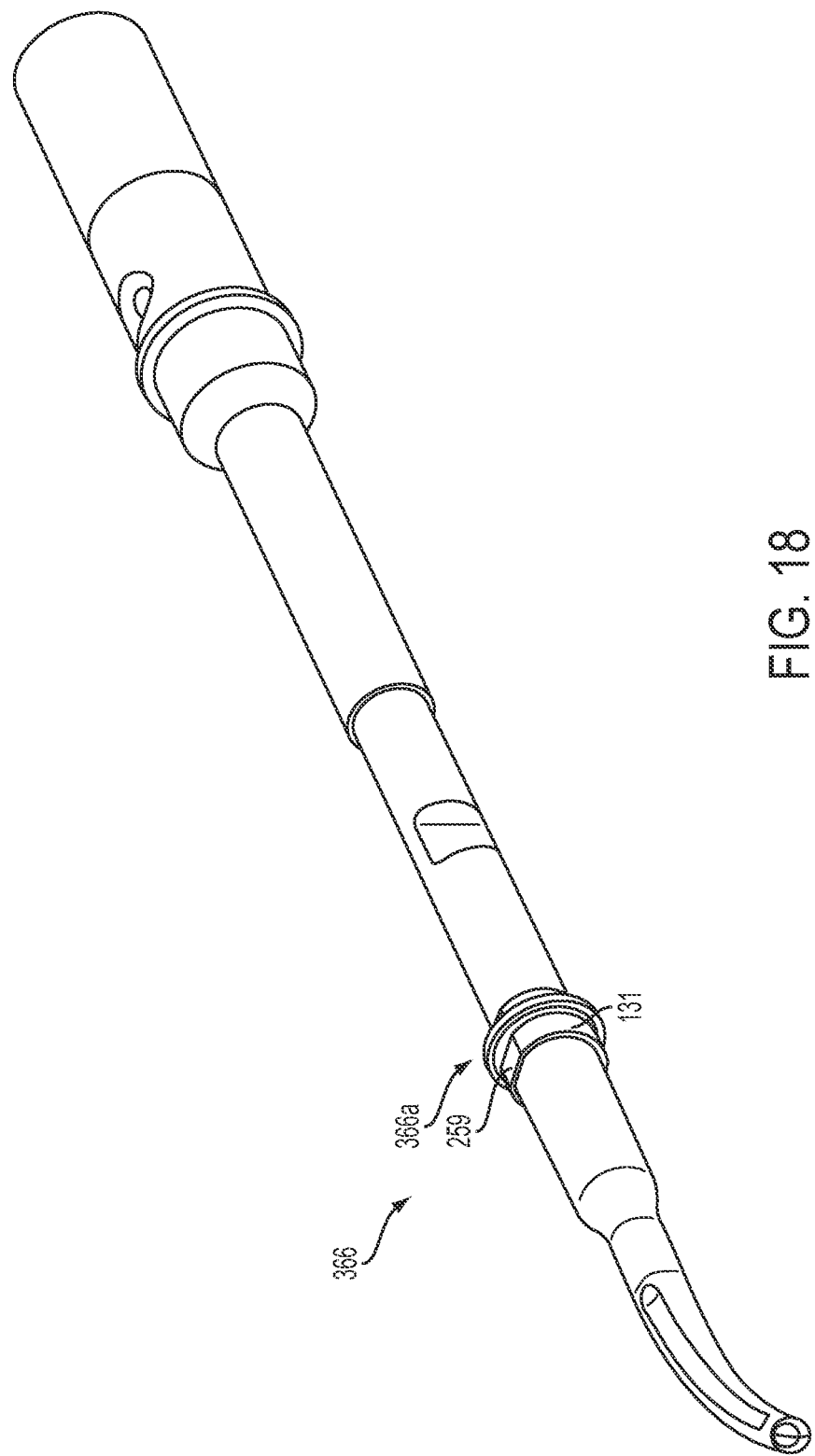
FIG. 18 illustrates a perspective view of a blade of the surgical instrument of FIG. 16.
Figure 19:
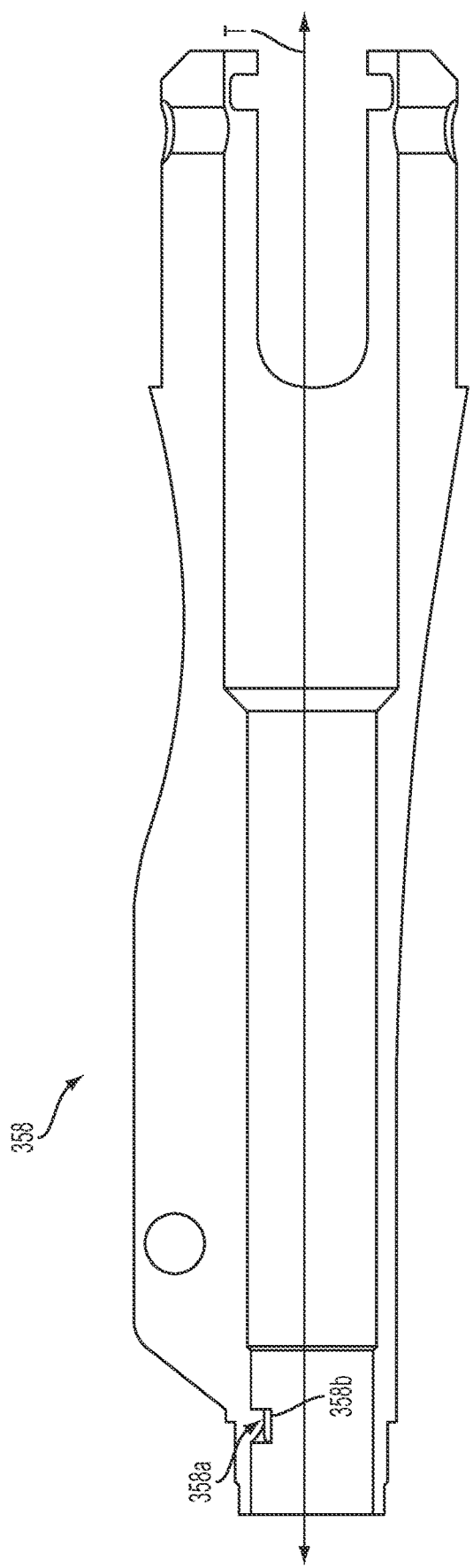
FIG. 19 illustrates a partial longitudinal cross-sectional view of a support shaft of the surgical instrument of FIG. 16.
Figure 20:
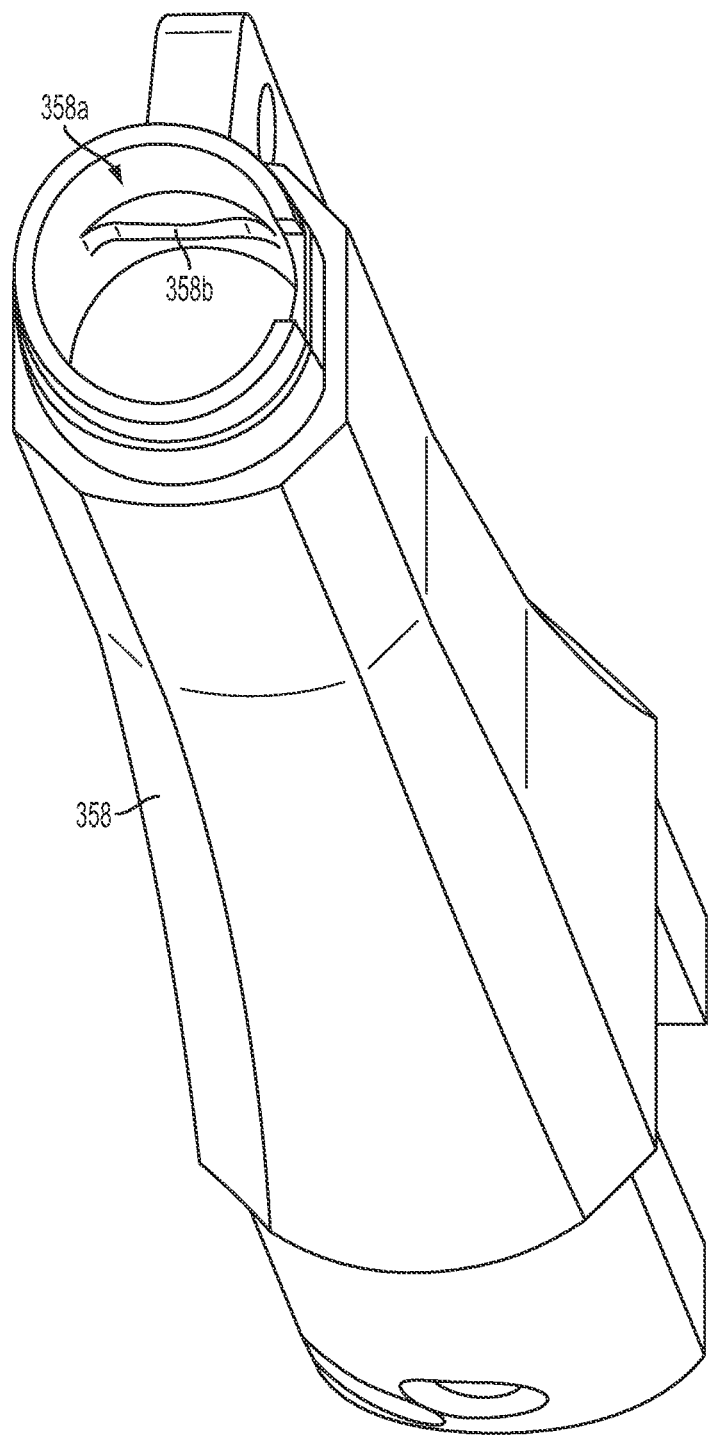
FIG. 20 illustrates a partial perspective view of the support shaft of FIG. 19.

In various instances, referring primarily to FIGS. 16-18, the alignment features 358a and/or 366a may be positioned at a node of vibration along the blade 366. As described above, a minimum or zero crossing in the vibratory motion may exist at a node of vibration; positioning the alignment features 358a and/or 366a at the node of vibration may reduce interference with the operation of the blade 366, which may increase the efficiency of the ultrasonic energy transmission, for example. In certain instances, the alignment features 358a and/or 366a may be positioned at a distal node of vibration. In certain instances, the alignment features 358a and/or 366a may be positioned at a node closest to the distal end of the blade 366, for example.

In various instances, referring to FIGS. 16-18, the alignment feature 358a and/or the alignment feature 366a may comprise one or more vibration isolating portions 259 such as, for example, an overmolded silicone rubber bushing. In various instances, the vibration isolating portions 259 can be overmolded onto the blade 366 and/or the support shaft 358, for example. In certain instances, the vibration isolating portions 259 can be integrated with the sealing member 131. As illustrated in FIG. 17, the sealing member 131 can be disposed between the blade 366 and support shaft 358. In certain instances, the sealing member 131 can be disposed around, or at least partially around, the blade 366, for example. In certain instances, the sealing member 131 may be positioned at or adjacent to a distal node of vibration. In certain instances, the sealing member 131 may be positioned at or adjacent to a node closest to the distal end of the blade 366, for example. In various instances, the sealing member 131 may comprise a sealing lip or a ring disposed around the blade 366, for example.

In certain instances, as illustrated in FIGS. 17-20, the alignment feature 358a may comprise a flat section 358b which can be aligned with a corresponding flat section 366b of the blade 266 to establish rotational alignment between the blade 366 and the support shaft 358 and maintain such alignment during use of the surgical instrument 310 in a surgical procedure, for example. In certain instances, the greater the surface areas of the interfacing flat sections 358b and/or 366b, the more robust the alignment achieved therebetween. In at least one example, one or both of the surface areas of the interfacing flat sections 358b and/or 366b may comprise a multilateral shape such as a square, for example. In at least one example, one or both of the surface areas of the interfacing flat sections 358b and/or 366b may comprise a circular shape.

In various instances, as described above, the support shaft 358 can be pivotably coupled to the clamp member 364 such that actuation of the handle 301 may cause the clamp member 364 to transition between an open configuration and an approximated configuration to capture tissue between the clamp member 364 and the blade 366, for example. In such instances, the clamp member 364 may generate a clamping force against the blade 366.

In certain instances, the clamping force generated by the clamp member 364 can be applied along a vector which intersects a plane P defined by the flat section 366b of the blade 366, for example. In certain instances, the vector of the generated clamping force can form a perpendicular, or at least substantially perpendicular, angle with the plane P, for example. In certain instances, the angle between the vector of the generated clamping force and the plane P defined by the flat section 366b of the blade 366 can be any value selected from a range of about 85 degrees to about 95 degrees. In certain instances, the angle between the vector of the generated clamping force and the plane P defined by the flat section 366b of the blade 366 can be any value selected from a range of about 89 degrees to about 91 degrees.

In various instances, as illustrated in FIG. 16, the clamp member 364 can be movable between the open configuration and the closed configuration along, or at least substantially along, a plane P1 intersecting the plane P defined by the flat section 366b of the blade 366. In certain instances, the plane P1 can be perpendicular, or at least substantially perpendicular with the plane P. In certain instances, the angle between the plane P1 and the plane P is any angle selected from a range of about 85 degrees to about 95 degrees. In certain instances, the angle between the plane P1 and the plane P is any angle selected from a range of about 89 degrees to about 91 degrees.

In various instances, referring primarily to FIGS. 16 and 18, the clamp member 364 and the flat section 358b of the support shaft 358 can be disposed on opposite sides of the plane P defined by the flat section 366b of the blade 366, for example. In such instances, the clamping force generated by the clamp member 364 may bias, motivate, and/or move the alignment feature 366a of the blade 266 toward the alignment feature 358a of the support shaft 358. In certain instances, the clamping force generated by the clamp member 364 may bring the alignment feature 366a of the blade 366 into contact with the alignment feature 358a of the inner tube 358. As illustrated in FIG. 17, in certain instances, a slight rotational misalignment may remain after assembly of the surgical instrument 310. Such slight rotational misalignment is, however, corrected when the alignment feature 366a of the blade 266 is biased toward the alignment feature 358a of the support shaft 358 by the application of the clamping force generated by the clamp member 364 against the blade 366, for example.

As described above, the surgical instrument 10 (FIG. 2) may include a handle assembly such as, for example, the handle assembly 12 (FIG. 2), an end effector assembly such as, for example, the end effector assembly 26 (FIG. 2A), and an elongated shaft assembly such as, for example, the elongated shaft assembly 14 (FIG. 2) which extends between the handle assembly 12 and the end effector assembly 26. The handle assembly 12 may be adapted to receive the ultrasonic transducer 16 at the proximal end. The ultrasonic transducer 16 can be mechanically engaged to the elongated shaft assembly 14 and portions of the end effector assembly 26. Furthermore, the handle assembly 12 may comprise a trigger assembly such as, for example, the trigger assembly 24. As described above, the trigger assembly 24 may include a trigger 32 that operates in conjunction with a fixed handle 34.

Figure 21:
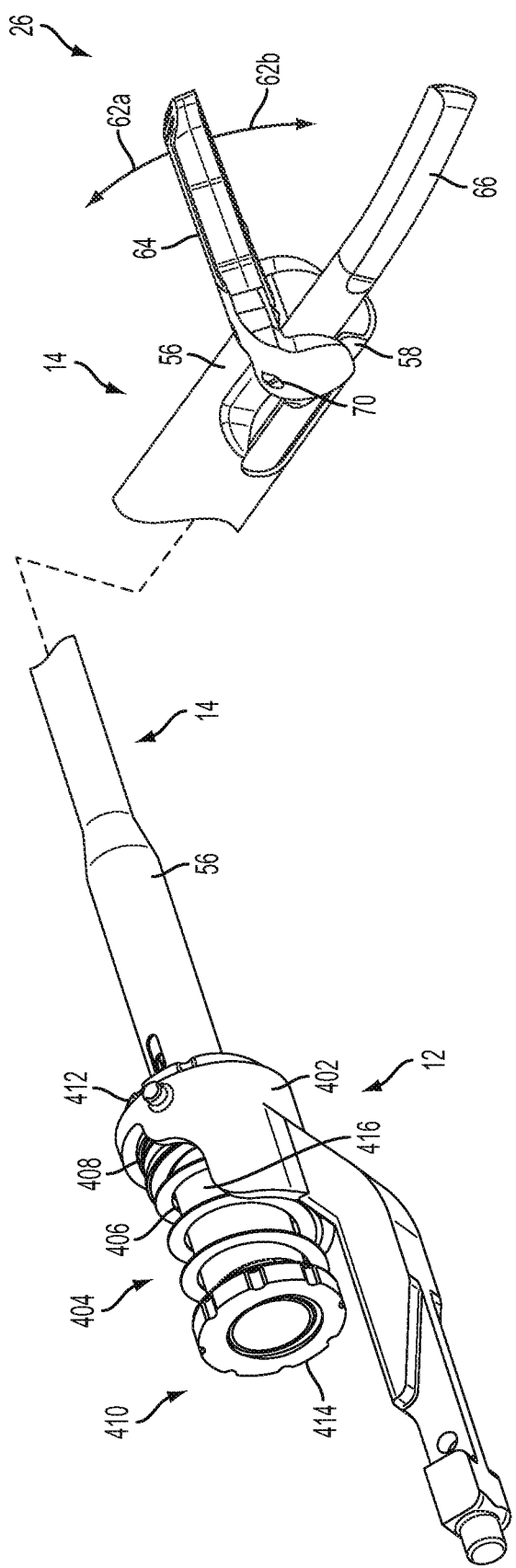
FIG. 21 illustrates a partial perspective view of the surgical instrument of FIG. 2 with several parts removed from the handle assembly to expose a load adjustment assembly and a reciprocating actuation member of the handle assembly of the surgical instrument of FIG. 2.

In various instances, the trigger 32 can be operably coupled to a reciprocating actuation member 402 (FIG. 21). In at least one example, a linkage assembly can be employed to couple the trigger 32 to the reciprocating actuation member 402. In certain instances, as illustrated in FIG. 21, the reciprocating actuation member 402 may be operably coupled to the clamp member 64. In at least one example, a drive shaft such as, for example, the outer tubular sheath 56 of the elongated shaft assembly 14 may be employed to transmit actuation motions from the reciprocating actuation member 402 to the clamp member 64, for example. The reader will appreciate that, in certain instances, the inner tubular member 158 of the elongated shaft assembly 114 can be employed as a drive shaft. In such instances, the inner tubular member 158 can be operably coupled to the reciprocating actuation member 402, for example.

Figure 21A:
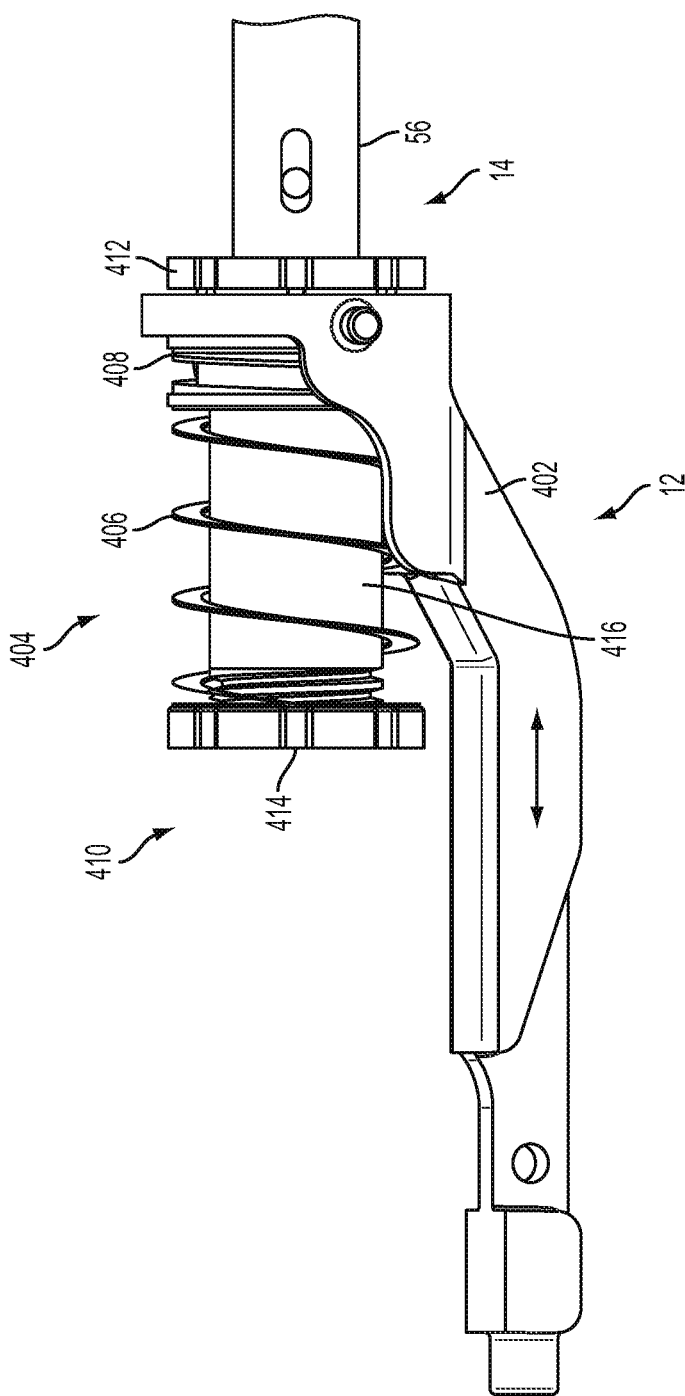
FIG. 21A illustrates the load adjustment assembly of FIG. 21 with the reciprocating actuation member at an unactuated position.
Figure 21B:
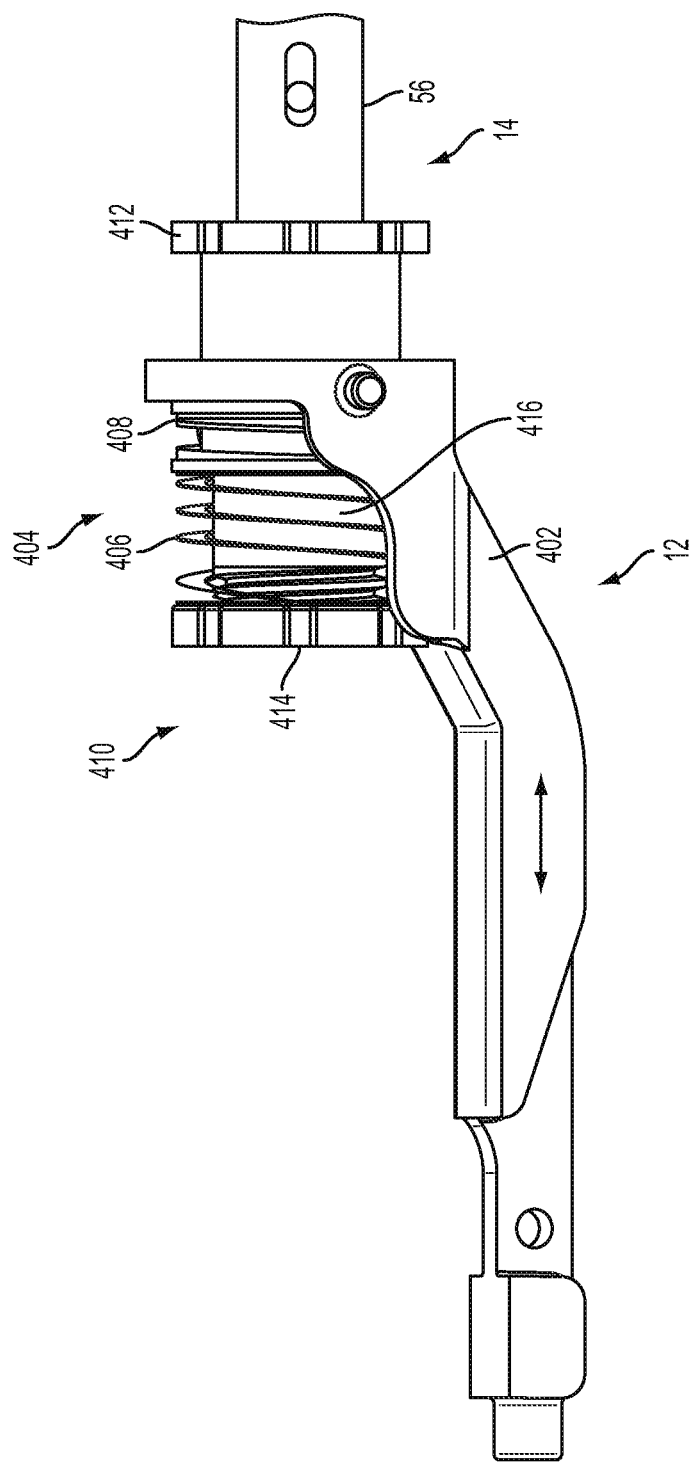
FIG. 21B illustrates the load adjustment assembly of FIG. 21 with the reciprocating actuation member at an actuated position.
Figure 22:
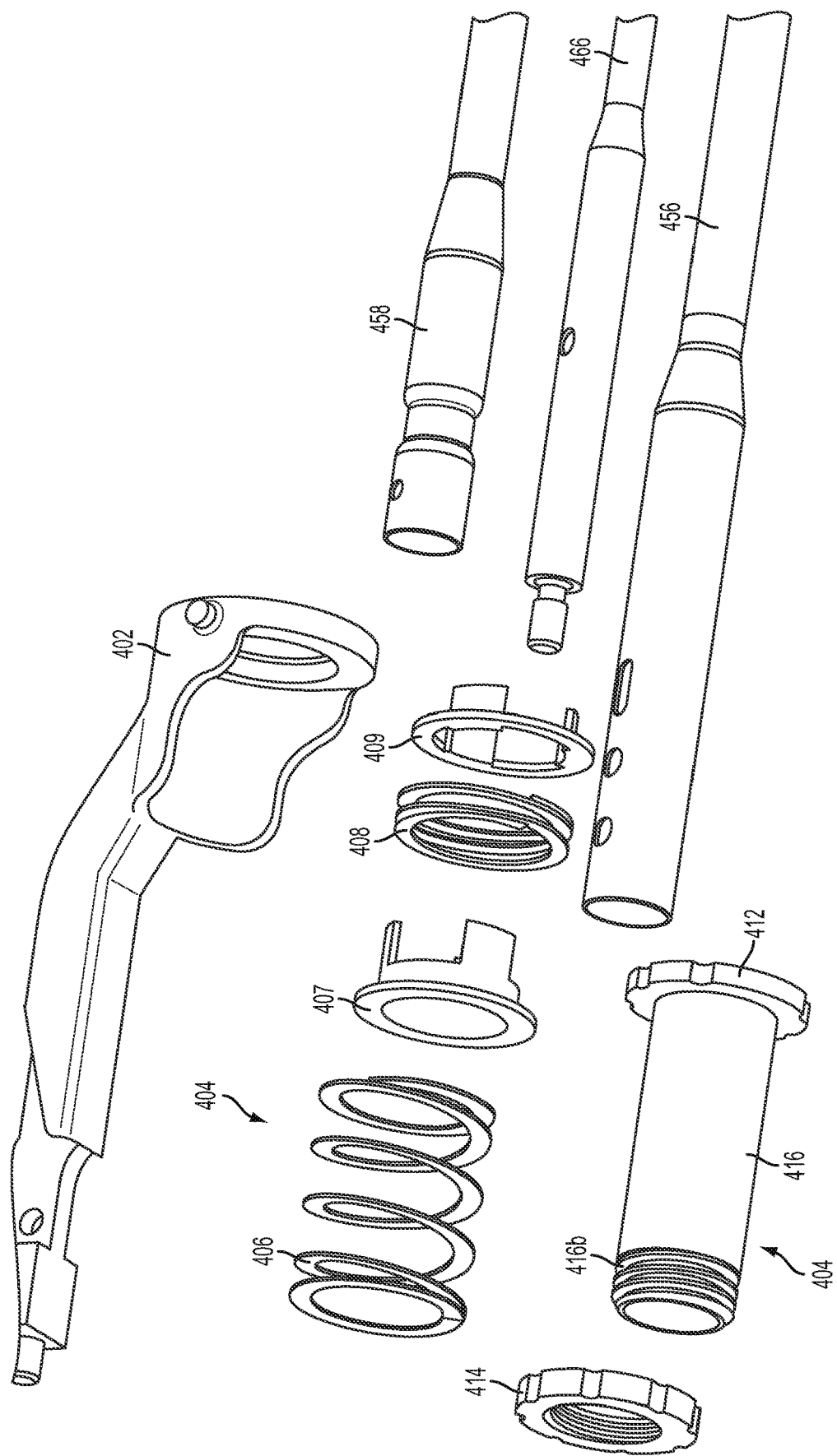
FIG. 22 illustrates a partial exploded view of the surgical instrument of FIG. 2.

In any event, the trigger 32 can be pivotally movable relative to the fixed handle 34 to reciprocate the reciprocating actuation member 402 between a first position, as illustrated in FIG. 21A, and a second position, as illustrated in FIG. 21B. In certain instances, the first position can be at a distal location to the second position, for example. In certain instances, the clamp member 64 can be transitioned between an open configuration and a closed configuration with respect to the ultrasonic blade 66 in response to the reciprocating motion of the reciprocating actuation member 402 between the first position and the second position, for example. In at least one example, the clamp member 64 can be in a fully open configuration while the reciprocating actuation member 402 is at the first position, as illustrated in FIG. 21. In at least one example, if the path of the clamp member 64 toward the ultrasonic blade 66 is not impeded, the clamp member 64 can be in a fully closed configuration while the reciprocating actuation member 402 is at the second position.

In certain instances, the trigger 32 can be pivotally movable in the direction 33A toward the fixed handle 34 to transition the reciprocating actuation member 402 toward the second position and transition the clamp member 64 toward the closed configuration. In certain instances, the trigger 32 can be pivotally movable in the direction 33B away from the fixed handle 34 to transition the reciprocating actuation member 402 toward the first position and transition the clamp member 64 toward the closed configuration, for example.

In certain instances, a biasing mechanism 404 may cause the trigger 32 to pivotally move in the direction 33B when the user releases the squeezing force against the trigger 32. The biasing mechanism 404 may bias the reciprocating actuation member 402 toward the first position and bias the clamp member 64 toward the open configuration, as illustrated in FIG. 21A. In certain instances, the biasing mechanism 404 may comprise one or more springs. In at least one example, the biasing mechanism 404 may include a proximal spring 406, for example, and/or a distal spring 408, for example, as illustrated in FIG. 21.

In various instances, the biasing mechanism 404 may be configured to apply an initial load to the reciprocating actuation member 402 to maintain the reciprocating actuation member 402 at the first position; in turn, the reciprocating actuation member 402 maintains the clamp member 64 in the open configuration, as illustrated in FIG. 21. The reader will appreciate that the initial load applied by the biasing mechanism 404 against the reciprocating actuation member 402 defines, at least in part, an initial force required to overcome the initial load to motivate the reciprocating actuation member 402 from the first position toward the second position and motivate the clamp member 64 from the open configuration toward the closed configuration, for example.

The reader will also appreciate that accurately and reproducibly setting and maintaining the initial load ensures uniformity of the initial force required to overcome the initial load. Such uniformity aids a user of the surgical instrument 10 in developing a type of tactile memory when squeezing the trigger 32 to generate the initial force. In other words, eliminating, or at least reducing, variability of the initial load provides a user of the surgical instrument 10 with an element of predictability in using the trigger 32 that facilitates developing a tactile memory associated with squeezing the trigger 32, for example. Furthermore, accurately and reproducibly setting and maintaining the initial load ensures that the surgical instrument 10 produces a consistent and optimized clamp force on tissue, which creates consistent and optimum hemostasis and tissue effects.

In various instances, the handle assembly 12 may comprise a load adjustment assembly 410, which can be employed to set and maintain the initial load against the reciprocating actuation member 402 at a predetermined value. In certain instances, as illustrated in FIG. 21, the load adjustment assembly 410 can be coupled to a drive shaft of the surgical instrument 10 such as, for example, the outer tubular sheath 56 or inner tubular member 158. The load adjustment assembly 410 may include a stop 412 and a load adjustment member 414. In certain instances, the stop 412 can be disposed at a distal location relative to the load adjustment member 414, for example. In at least one example, the stop 412 can be disposed at a proximal location to the load adjustment member 414.

In certain instances, as illustrated in FIG. 21, the biasing mechanism 404 can be disposed between the stop 412 and the load adjustment member 414. The reciprocating actuation member 402 can be disposed between the stop 412 and the biasing mechanism 404. In certain instances, the reciprocating actuation member 402 is abutted against the stop 412 at the first position, as illustrated in FIG. 21A. In certain instances, as described above, the biasing mechanism 404 may include a proximal spring 406 and a distal spring 408. A first washer 407 can be disposed between the proximal spring 407 and the distal spring 408, for example. A second washer 409 can be disposed between the distal spring 408 and the reciprocating actuation member 402, for example. Other relative positions and/or arrangements of the stop 412, the load adjustment member 414, and the biasing mechanism 404 with respect to each other are contemplated by the present disclosure.

In various instances, the distance between the stop 412 and the load adjustment member 414 can determine the initial load against the reciprocating actuation member 402. In certain instances, the load adjustment member 414 is movable relative to the stop 412 to adjust the initial load applied against the reciprocating actuation member 402 to the predetermined value by adjusting the distance between the stop 412 and the load adjustment member 414. In certain instances, upon reaching the predetermined value of the initial load, the load adjustment member 414 is fixed in position relative to the stop 412, as described below in greater detail, to fix the distance between the stop 412 and the load adjustment member 414.

In certain instances, movement of the load adjustment member 414 relative to the stop 412 motivates the springs 406 and/or 408 of the biasing mechanism 404 to change the load applied by the biasing mechanism 404 against the reciprocating actuation member 402. In at least one example, movement of the load adjustment member 414 toward the stop 412 compresses the springs 406 and/or 408 of the biasing mechanism 404 which increases the initial load applied by the biasing mechanism 404 against the reciprocating actuation member 402. In at least one example, movement of the load adjustment member 414 away from the stop 412 at least partially decompresses the springs 406 and/or 408 of the biasing mechanism 404 which decreases the initial load applied by the biasing mechanism 404 against the reciprocating actuation member 402.

Figure 23:
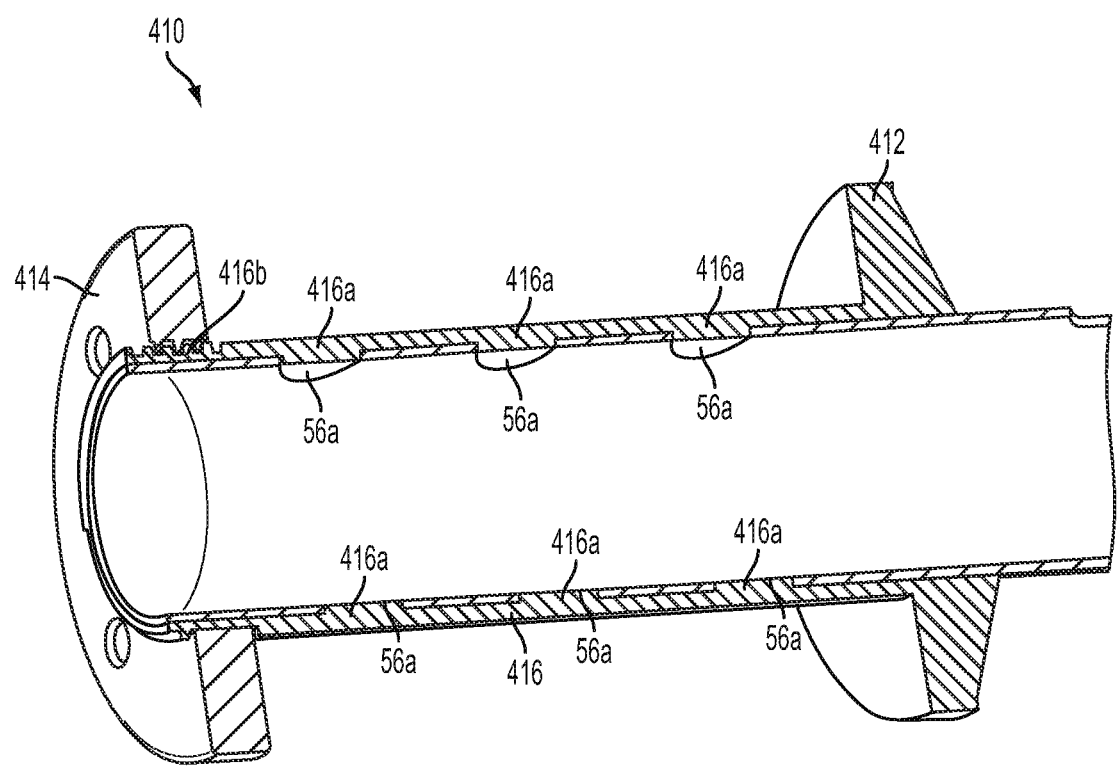
FIG. 23 illustrates a partial longitudinal cross-sectional view of a collar, and a load adjustment member of the load adjustment assembly of FIG. 21.

In certain instances, the load adjustment assembly 410 may include a collar 416. The collar 416 can be attached to a drive shaft of the surgical instrument 10 such as, for example, the outer tubular sheath 56 or the inner tubular member 158. FIG. 23 shows the collar 416 assembled with the outer tubular sheath 56. As illustrated in FIG. 23, the collar 416 may comprise a cylindrical, or at least substantially cylindrical, shape which can be disposed around the outer tubular sheath 56, for example. In certain instances, as illustrated in FIG. 23, the collar 416 may comprise a plurality of mating members 416A configured form mating engagement with a plurality of corresponding openings 56A of the outer tubular sheath 56, for example. As illustrated in FIG. 23, the matting members 416A may be disposed on an inner wall of the collar 416. In at least one example, the collar 416 can be glued to the outer tubular sheath 56. In another example, the collar 416 can be welded onto the outer tubular sheath 56. Other techniques for attaching the collar 416 to the outer tubular sheath 56 are contemplated by the present disclosure.

As illustrated in FIG. 23, the collar 416 can be attached to a proximal portion of the outer tubular sheath 56. In certain instances, the collar 416 and the stop 412 can be manufactured as a single unit. The stop 412 may be comprised of a flange positioned at a distal end of the collar 416, for example. In certain instances, the load adjustment member 414 can be coupled to the collar 416. For example, the collar 416 may include a threaded proximal portion 416b which can be configured to receive the load adjustment member 414. The load adjustment member 414 can, for example, be threadedly engaged with the threaded proximal portion 416b, as illustrated in FIG. 23. In such instances, rotation of the load adjustment member 414 relative to the collar 416 in a first direction, for example a clockwise direction, may advance the load adjustment member 414 toward the stop 412, and rotation of the load adjustment member 414 relative to the collar 416 in a second direction, for example a counterclockwise direction, may retract the load adjustment member 414 away from the stop 412. Advancement of the load adjustment member 414 toward the stop 412 may compress the springs 406 and/or 408 thereby increasing the load applied against the reciprocating actuation member 402. On the other hand, retraction of the load adjustment member 414 away from the stop 412 may allow the springs 406 and/or 408 to at least partially decompress thereby reducing the load applied against the reciprocating actuation member 402.

In certain instances, to set the initial load applied against the reciprocating actuation member 402 to a predetermined value, a load monitoring unit can be employed. The load exerted by the biasing mechanism 404 against the reciprocating actuation member 402 can be monitored by the load monitoring unit. Meanwhile, the load adjustment member 414 can be turned clockwise and/or counterclockwise, for example, to adjust the initial load to the predetermined value based on feedback from the load monitoring unit. Once the initial load is set to the predetermined value, in certain instances, a final position of the load adjustment member 414 can be fixed to maintain the initial load at the predetermined value. In certain instances, the final position of the load adjustment member 414 can be fixed by fixing the load adjustment member 414 to the collar 416. In at least one example, the final position of the load adjustment member 414 can be fixed by welding the load adjustment member 414 to the collar 416 at the final position. In at least one example, the final position of the load adjustment member 414 can be fixed by gluing the load adjustment member 414 to the collar 416 at the final position. Other techniques for fixing the load adjustment member 414 to the collar 416 at the final position are contemplated by the present disclosure.

Figure 24:
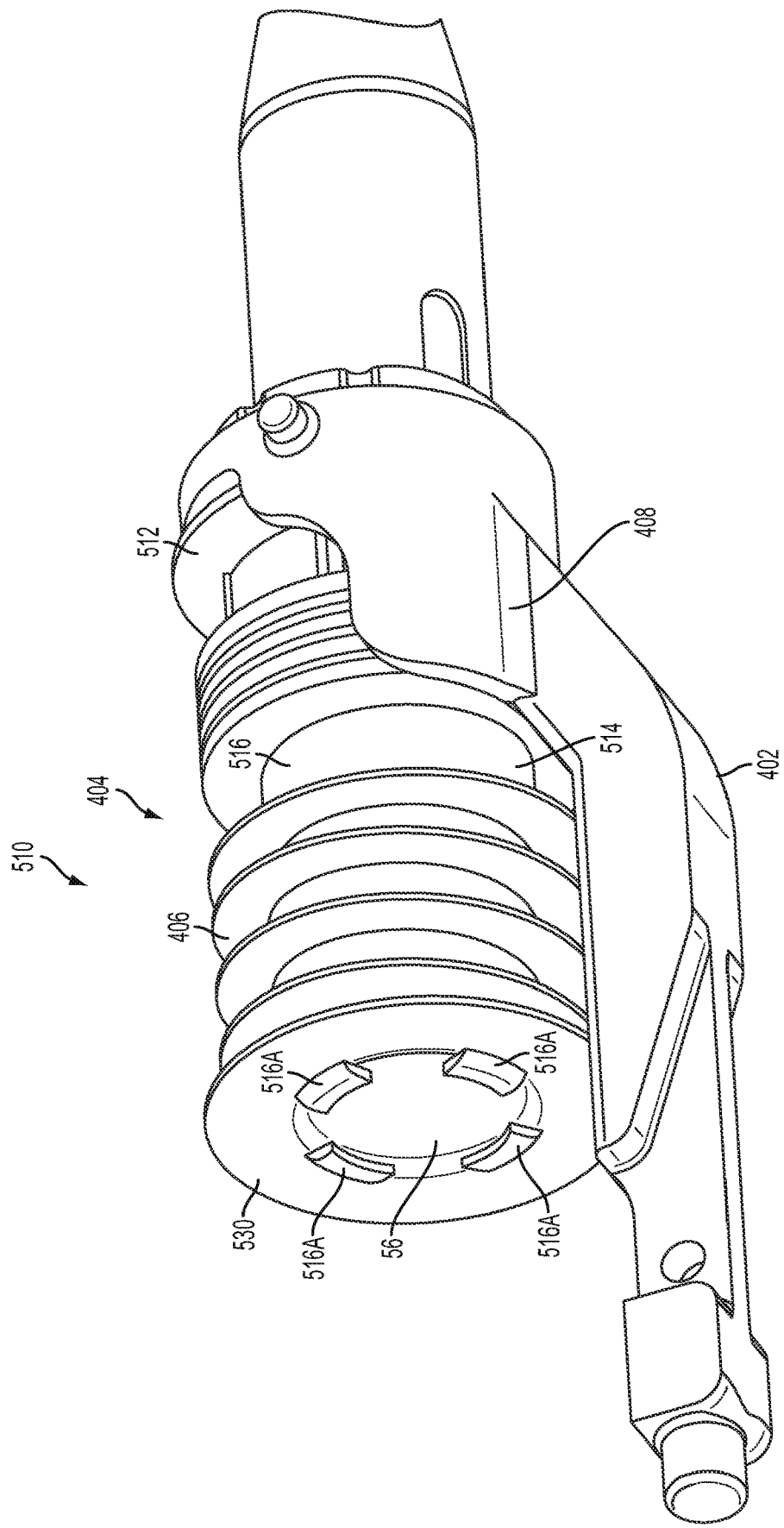
FIG. 24 illustrates a perspective view of a load adjustment assembly of the surgical instrument of FIG. 2.

Referring primarily to FIG. 24, in certain instances, the handle assembly 12 of the surgical instrument 10 may include a load adjustment assembly 510, which is similar in many respects to the load adjustment assembly 410. For example, the load adjustment assembly 510 includes the biasing mechanism 404. Also, like the load adjustment assembly 410, the load adjustment assembly 510 is operably coupled to a drive shaft of the surgical instrument 10 such as, for example, the outer tubular sheath 56 (FIG. 24) or the inner tubular member 158. Furthermore, like the load adjustment assembly 410, the load adjustment assembly 510 can be employed to adjust an initial load applied against a clamp member of the surgical instrument 10.

Referring to FIG. 24, the load adjustment assembly 510 may include a load adjustment member 514. The load adjustment member 514 may be comprised of a stop 512, a body portion 516, and a plurality of projections 516A extending proximally from the body portion 516. In certain instances, the stop 512 may be comprised of a flange member disposed at distal end of the body portion 516, as illustrated in FIG. 24. In certain instances, each of the plurality of projections 516A may be comprised of a tab extending proximally from the body portion 516, as illustrated in FIG. 25.

Figure 25:
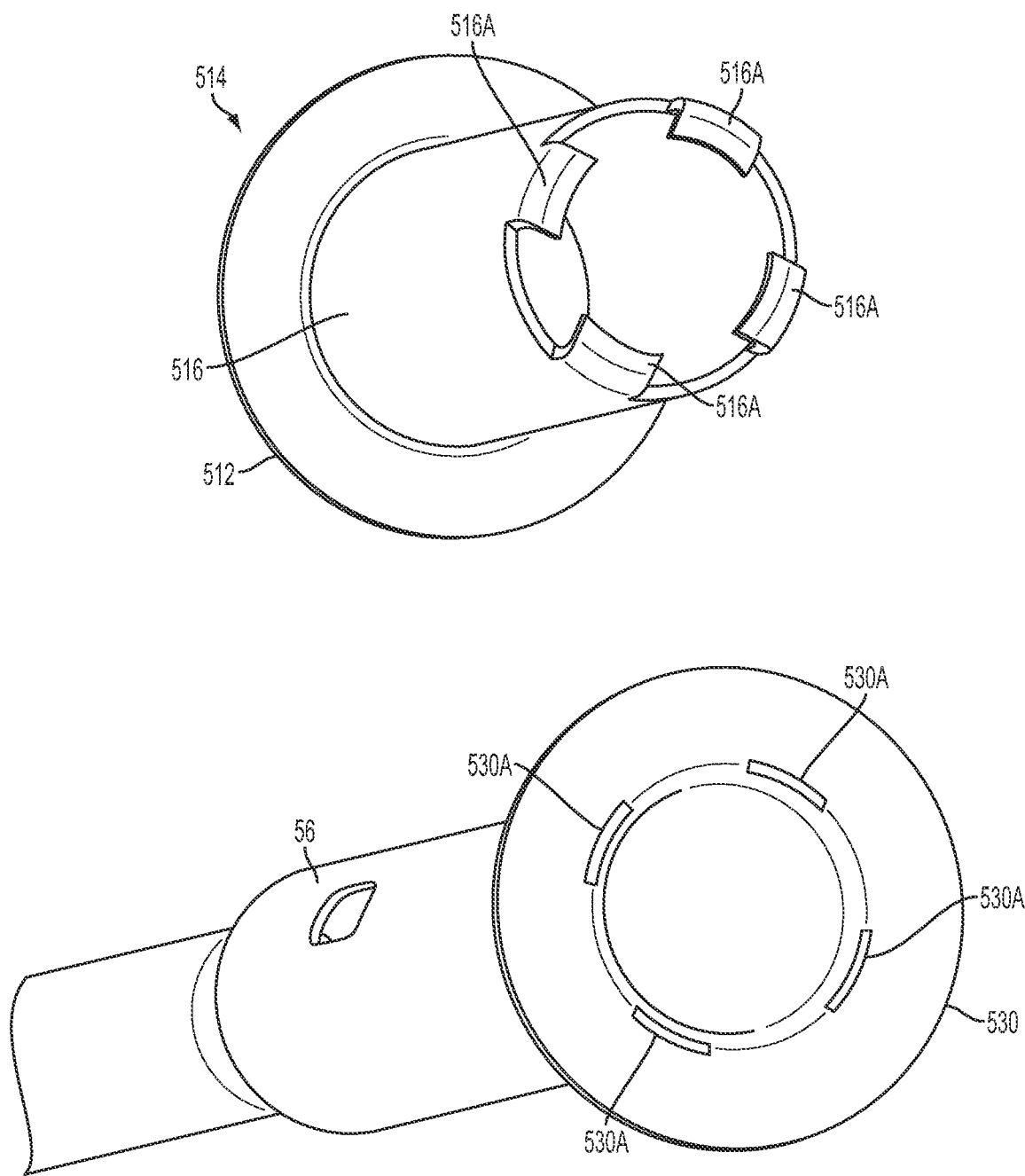
FIG. 25 illustrates is an exploded view of a collar, a drive shaft, and a load adjustment member of the load adjustment assembly of FIG. 24.

In certain instances, as illustrated in FIGS. 24 and 25, the body portion 516 of the load adjustment assembly 510 may comprise a cylindrical, or at least substantially cylindrical, shape which can be disposed around the drive shaft of the surgical instrument 10. For example, FIG. 24 shows the body portion 516 disposed around the outer tubular sheath 56.

Further to the above, as illustrated in FIG. 24, the load adjustment assembly 510 may also include a receiving end portion 530, which can be comprised of a flange member disposed at a proximal end of a drive shaft of the surgical instrument 10 such as, for example, the outer tubular sheath 56 or the inner tubular member 158. In certain instances, the receiving end portion 530 may comprise a plurality of slots 530A (FIG. 25), which can be configured to receive the projections 516A. In certain instances, the receiving end portion 530 can be integrated with the drive shaft of the surgical instrument 10. In certain instances, the receiving end portion 530 and the drive shaft of the surgical instrument 10 can be manufactured together as a single unit. In other instances, the receiving end portion 530 and the drive shaft of the surgical instrument 10 can be manufactured separately and attached to each other during assembly of the surgical instrument 10, for example.

In certain instances, as illustrated in FIG. 24, the biasing mechanism 404 can be disposed between the stop 512 and the receiving end portion 530. The reciprocating actuation member 402 can be disposed between the stop 512 and the biasing mechanism 404. Other relative positions and/or arrangements of the stop 512, the receiving end portion 530, and the biasing mechanism 404 with respect to each other are contemplated by the present disclosure.

As described above, in certain instances, the clamp member 64 can be transitioned between an open configuration and a closed configuration with respect to the ultrasonic blade 66 in response to the reciprocating motion of the reciprocating actuation member 402 between a first position and a second position, for example. In certain instances, the reciprocating actuation member 402 is abutted against the stop 512 at the first position.

In various instances, the distance between the stop 512 and the receiving end portion 530 of the load adjustment assembly 510 can determine the initial load against the reciprocating actuation member 402 at the first position. In certain instances, the load adjustment member 514 is slidably movable relative to the outer tubular sheath 56 to adjust the initial load applied against the reciprocating actuation member 402 to a predetermined value by adjusting the distance between the stop 512 and the receiving end portion 530. In certain instances, upon reaching the predetermined value of the initial load, the projections 516A are fixed to the receiving end portion 530 to fix the distance between the stop 512 and the receiving end portion 530.

In certain instances, movement of the load adjustment member 514 relative to the receiving end portion 530 motivates the springs 406 and/or 408 of the biasing mechanism 404 to change the load applied by the biasing mechanism 404 against the reciprocating actuation member 402. In at least one example, movement of the load adjustment member 514 toward the receiving end portion 530 compresses the springs 406 and/or 408 of the biasing mechanism 404 which increases the initial load applied by the biasing mechanism 404 against the reciprocating actuation member 402. In at least one example, movement of the load adjustment member 514 away from the receiving end portion 530 at least partially decompresses the springs 406 and/or 408 of the biasing mechanism 404 which decreases the initial load applied by the biasing mechanism 404 against the reciprocating actuation member 402.

In certain instances, to set the initial load to a predetermined value, a load monitoring unit can be employed. The load exerted by the biasing mechanism 404 against the reciprocating actuation member 402 can be monitored by the load monitoring unit. Meanwhile, the load adjustment member 514 can be slidably moved relative to the receiving end portion 530 to adjust the distance between stop 512 and the receiving end portion 530 based on feedback from the load monitoring unit until the predetermined value of the initial load is realized. As the load adjustment member 514 is moved relative to the outer tubular sheath 56, the projections 516A slide with respect to the slots 530A.

Once the initial load is set to the predetermined value, in certain instances, a final position of the load adjustment member 514 can be fixed to maintain the initial load at the predetermined value. In certain instances, the final position of the load adjustment member 514 can be fixed by fixing the projections 516A to the receiving end portion 530. In at least one example, the final position of the load adjustment member 514 can be fixed by bending or crimping the distal ends of the projection 516A that extend proximally beyond their corresponding slots 530A, as illustrated in FIG. 24. In certain instances, the distal ends of the projections 516A that extend proximally beyond their corresponding slots 530A can be welded to the receiving end portion 530 at the final position of the load adjustment member 514, for example. In at least one example, the distal ends of the projection 516A that extend proximally beyond their corresponding slots 530A can be glued to the receiving end portion 530 at the final position of the load adjustment member 514, for example. Other techniques for fixing the load adjustment member 514 to the receiving end portion 530 at the final position are contemplated by the present disclosure.

Figure 26:
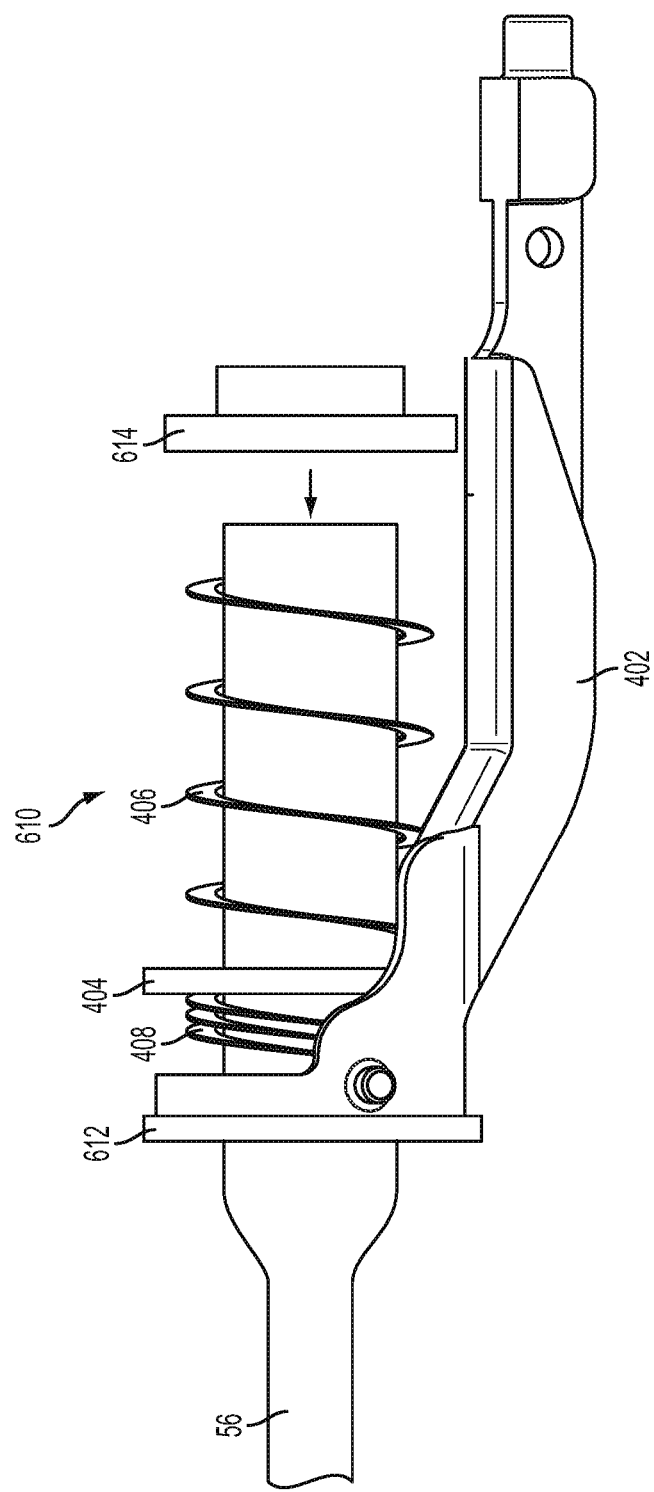
FIG. 26 illustrates a side-elevational view of a load adjustment assembly of the surgical instrument of FIG. 2 with an unattached load adjustment member.
Figure 26A:
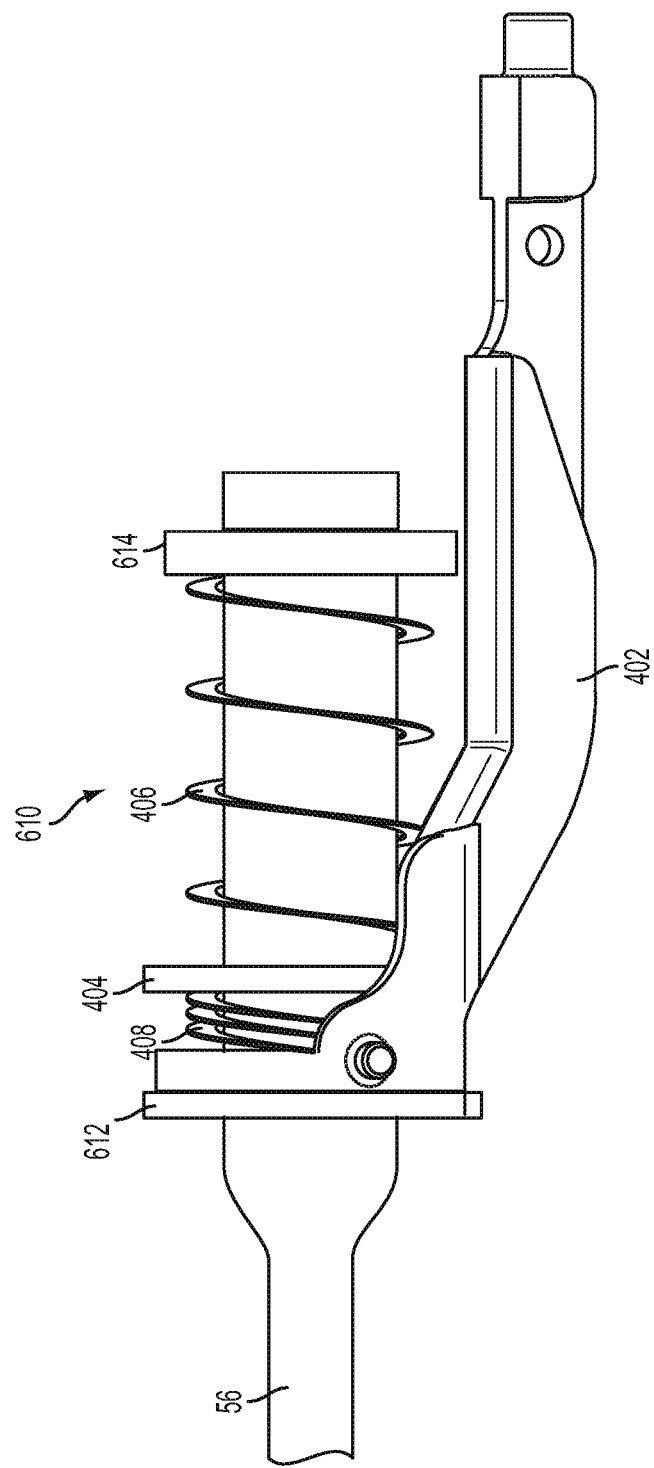
FIG. 26A illustrates a side-elevational view of the load adjustment assembly of the surgical instrument of FIG. 2 with an attached load adjustment member.

Referring primarily to FIGS. 26 and 26A, in certain instances, the handle assembly 12 of the surgical instrument 10 may include a load adjustment assembly 610, which is similar in many respects to the load adjustment assemblies 410 and/or 510. For example, the load adjustment assembly 610 includes the biasing mechanism 404. Also, like the load adjustment assemblies 410 and 510, the load adjustment assembly 610 is operably coupled to a drive shaft of the surgical instrument 10 such as, for example, the outer tubular sheath 56 or the inner tubular member 158. Furthermore, like the load adjustment assemblies 410 and 510, the load adjustment assembly 610 can be employed to adjust an initial load applied against a clamp member of the surgical instrument 10.

Referring to FIGS. 26 and 26A, the load adjustment assembly 610 may include a stop 612 and a load adjustment member 614. In certain instances, the stop 612 may be comprised of a flange member disposed around, or at least partially around, a proximal portion of a drive shaft of the surgical instrument 10 such as, for example, the outer tubular sheath 56 and the inner tubular member 158. For example, FIG. 26 shows the stop 612 disposed around a proximal portion of the outer tubular sheath 56.

In certain instances, as illustrated in FIG. 26A, the load adjustment member 614 may be assembled with the outer tubular sheath 56 such that the biasing mechanism 404 is disposed between the stop 612 and the load adjustment member 614. In certain instances, the load adjustment member 614 may comprise a cylindrical, or at least substantially cylindrical, shape which can be slidably inserted around a proximal end of the drive shaft of the surgical instrument 10. For example, FIG. 26A shows the load adjustment member 614 disposed around the proximal portion of the outer tubular sheath 56. In certain instances, the stop 612 can be disposed at a distal location relative to the load adjustment member 614, for example. Alternatively, the stop 612 can be disposed at a proximal location relative to the load adjustment member 614. The reciprocating actuation member 402 can be disposed between the stop 612 and the biasing mechanism 404. In certain instances, the reciprocating actuation member 402 is abutted against the stop 612 at the first position, as illustrated in FIG. 26A. Other relative positions and/or arrangements of the stop 612, the load adjustment member 614, and the biasing mechanism 404 with respect to each other are contemplated by the present disclosure.

In various instances, the relative distance between the stop 612 and the load adjustment member 614 can determine the initial load against the reciprocating actuation member 402. In certain instances, the load adjustment member 614 is slidably movable relative to the stop 612 to adjust the initial load applied against the reciprocating actuation member 402 to the predetermined value by adjusting the distance between the stop 612 and the load adjustment member 614. In certain instances, upon reaching the predetermined value of the initial load, the load adjustment member 614 is fixed in position relative to the stop 612, as described below in greater detail, by fixing the distance between the stop 612 and the load adjustment member 614.

In certain instances, movement of the load adjustment member 614 relative to the stop 612 motivates the springs 406 and/or 408 of the biasing mechanism 404 to change the load applied by the biasing mechanism 404 against the reciprocating actuation member 402. In at least one example, movement of the load adjustment member 416 toward the stop 612 compresses the springs 406 and/or 408 of the biasing mechanism 404, which increases the initial load applied by the biasing mechanism 404 against the reciprocating actuation member 402. In at least one example, movement of the load adjustment member 614 away from the stop 612 at least partially decompresses the springs 406 and/or 408 of the biasing mechanism 404, which decreases the initial load applied by the biasing mechanism 404 against the reciprocating actuation member 402.

In certain instances, to set the initial load to a predetermined value, a load monitoring unit can be employed. The load exerted by the biasing mechanism 404 against the reciprocating actuation member 402 can be monitored by the load monitoring unit. Meanwhile, the load adjustment member 614 can be slidably moved relative to the stop 612 to adjust the distance between the load adjustment member 614 and the stop 612 until the predetermined value of the initial load is realized. Once the initial load is set to the predetermined value, in certain instances, a final position of the load adjustment member 614 can be fixed to maintain the initial load at the predetermined value by fixing the distance between the load adjustment member 614 and the stop 612. In certain instances, the final position of the load adjustment member 614 can be fixed by fixing the load adjustment member 614 to the outer tubular sheath 56. In at least one example, the final position of the load adjustment member 614 can be fixed by welding the load adjustment member 614 to the outer tubular sheath 56 at the final position. In at least one example, the final position of the load adjustment member 614 can be fixed by gluing the load adjustment member 614 to the outer tubular sheath 56 at the final position. Other techniques for fixing the load adjustment member 614 to the outer tubular sheath 56 at the final position are contemplated by the present disclosure.

Figure 27:
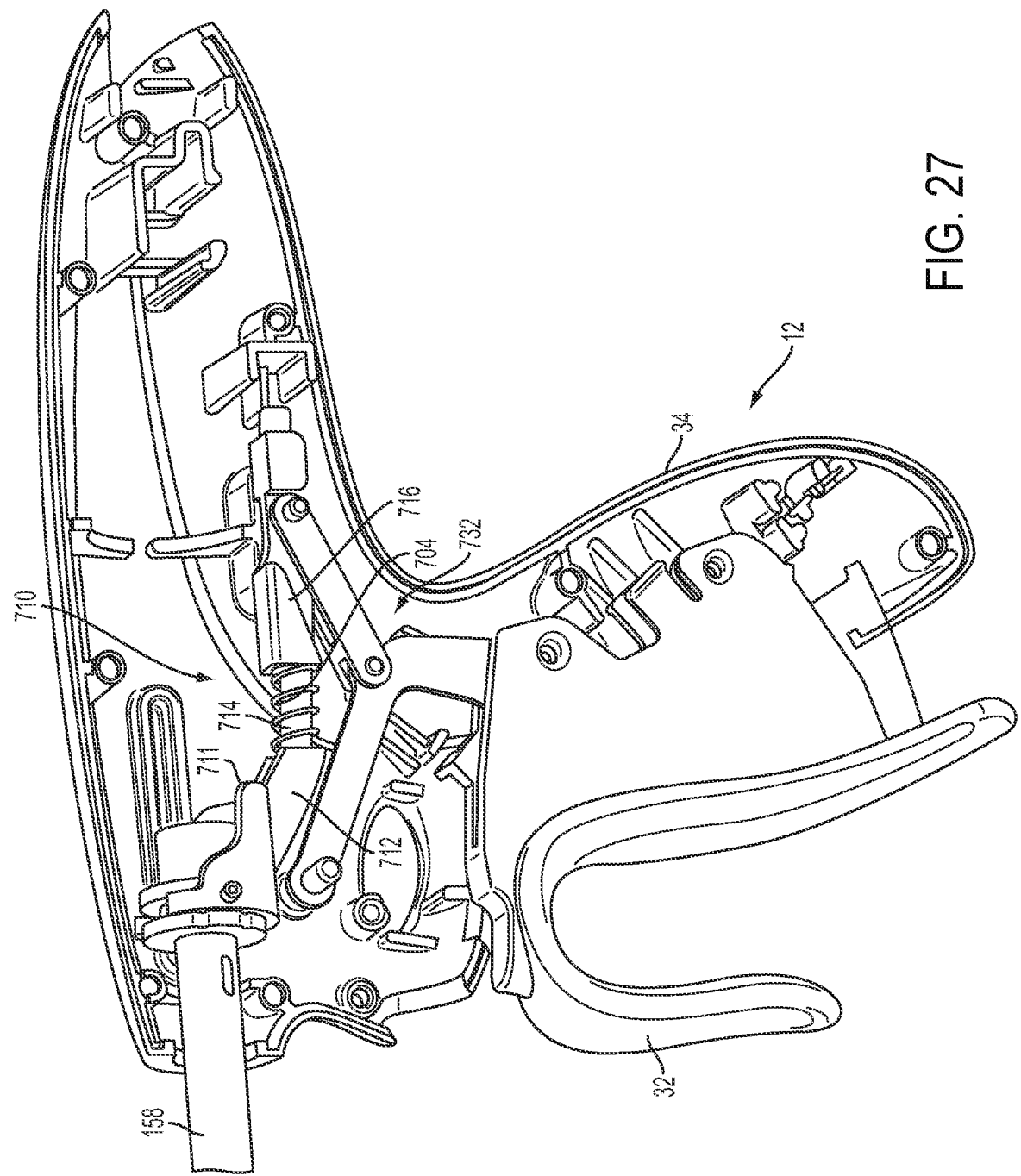
FIG. 27 illustrates a perspective of a handle assembly of the surgical instrument of FIG. 2, wherein a left shell of the handle assembly is removed to expose a load adjustment assembly.

Referring primarily to FIG. 27, in certain instances, the handle assembly 12 of the surgical instrument 10 may include a load adjustment assembly 710, which is similar in many respects to the load adjustment assemblies 410, 510, and/or 610. For example, like the load adjustment assemblies 410, 510, and 610, the load adjustment assembly 710 is operably coupled to a drive shaft of the surgical instrument 10 such as, for example, the outer tubular sheath 56 or the inner tubular member 158. Furthermore, the load adjustment assembly 710 can be employed to adjust an initial load (a pre-load) applied against a biasing member 704. As described in greater detail below, the biasing member 704 can be configured to protect from transmission of excessive actuation forces greater than the pre-load to a clamp member of the surgical instrument 10.

Referring to FIG. 27, the load adjustment assembly 710 may include a distal yoke portion 712, a proximal yoke portion 716, and a load adjustment member 714 extending between the distal yoke portion 712 and the proximal yoke portion 716. In certain instances, the biasing member 704 may comprise a tension spring which can be located at least partially around the load adjustment member 714, as illustrated in FIG. 27. In certain instances, a distal end of the biasing member 704 can be connected to the distal yoke portion 712 and a proximal end of the biasing member 704 can be connected to the proximal yoke portion 716.

Further to the above, the distal yoke portion 712 can be operably coupled to a drive shaft of the surgical instrument 10 such as, for example, the outer tubular sheath 56 or the inner tubular member 158. FIG. 27 shows a drive collar 711 coupling the distal yoke portion 712 to the inner tubular member 158. In addition, the proximal yoke portion 716 may be operably coupled to the trigger 32 of the handle assembly 12. For example, a linkage assembly 732 may couple the trigger 32 to the proximal yoke portion 716, as illustrated in FIG. 27.

In certain instances, the trigger 32 can be pivotably moved relative to the fixed handle 34 to reciprocate the inner tubular member 158 axially between a first position and a second position. As described above, the inner tubular member 158 can be pivotably coupled to a clamp member such as, for example, the clamp member 164. In certain instances, the first position can be at a distal location to the second position, for example. In certain instances, the clamp member 164 can be transitioned between an open configuration and a closed configuration with respect the ultrasonic blade 66 in response to the reciprocating motion of the inner tubular member 158 between the first position and the second position, for example. In at least one example, the clamp member 164 can be in a fully open configuration while the inner tubular member 158 is at the first position. In at least one example, if the path of the clamp member 164 toward the ultrasonic blade 66 is not impeded, the clamp member 164 can be in a fully closed configuration while the inner tubular member 158 is at the second position.

In use, the trigger 32 can be pivoted toward the fixed handle 34 to apply a force to the load adjustment assembly 710 to transition the load adjustment assembly 710 and the inner tubular member 158 proximally thereby causing the clamp member 164 to be actuated toward the closed configuration, for example. In certain instances, the force applied to the clamp member 164 of the surgical instrument 10 by pivotal movement of the trigger 32 acting through the load adjustment assembly 710 can be limited, or at least partially limited, by the biasing member 704. In certain instances, the biasing member 704 can be a tension coil spring which can be stretched between the proximal yoke portion 716 and the distal yoke portion 712 to set a biasing member pre-load to a predetermined value. The pre-load can be adjusted to the predetermined value by employing the load adjustment member 714 to adjust the distance between the proximal yoke portion 716 and the distal yoke member 712, as described in greater detail below.

In certain instances, the biasing member 704 may limit force transmission from the trigger 32 to the clamp member 164 if excessive force is applied to the trigger 32 by a user of the surgical instrument 10. When the force, which is applied by the user to the trigger 32, is less than the pre-load limit of the biasing member 704, the load adjustment assembly 710 moves as a single unit to reciprocate the inner tubular member 158 and actuate the clamp member 164. In other words, a force less than the pre-load limit of the biasing member 704 does not result in relative motion between the proximal yoke portion 716 and the distal yoke portion 712.

However, when the force, which is applied by the user to the trigger 32, exceeds the pre-load limit of the biasing member 704, the biasing member 704 may be further stretched between the proximal yoke portion 716 and the distal yoke portion 712 thereby causing the proximal yoke portion 716 to move independently from the distal yoke portion 712 for a limited degree thereby limiting the transmission of the excessive force to the inner tubular member 158 and the clamp member 164.

Figure 28:
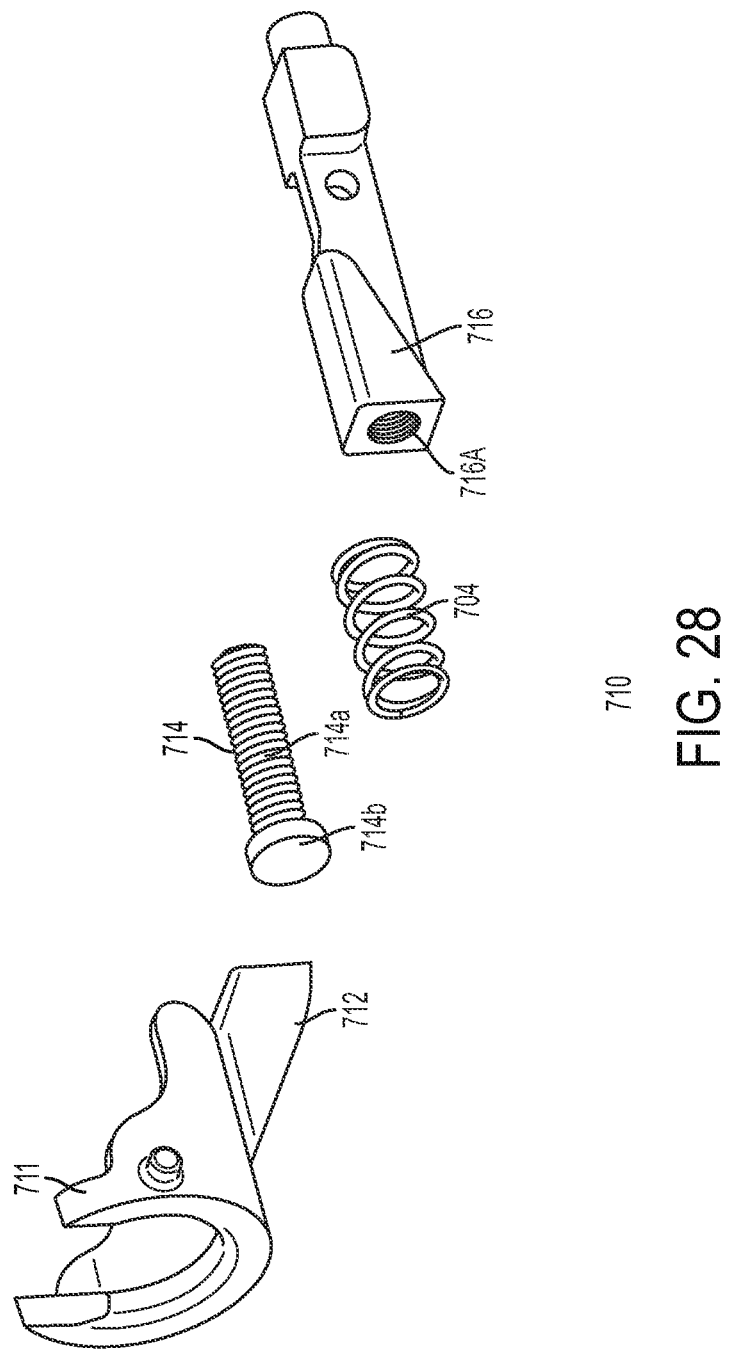
FIG. 28 illustrates an exploded view of a load adjustment assembly of the handle assembly of FIG. 27.

In certain instances, as illustrated in FIG. 28, the load adjustment member 714 may comprise a threaded proximal portion 714A and a distal stop 714B. The distal stop 714B can be abutted against the distal yoke portion 712. The threaded proximal portion 714A can be received, or at least partially received, within a receiving portion 716A of the proximal yoke portion 716. For example, the receiving portion 716A may include a thread on an internal wall of the receiving portion 716A which can be threadedly engaged with the threaded proximal portion 714A, for example.

The load adjustment member 714 can be employed to stretch the tension spring of the biasing member 704 between the proximal yoke portion 716 and the distal yoke portion 712 to an initial stretched condition corresponding to a desired pre-load by adjusting the distance between the proximal yoke portion 716 and the distal yoke portion 712. For example, rotation of the load adjustment member 714 relative to the proximal yoke portion 716 in a first direction, for example a clockwise direction, may cause the proximal yoke portion 716 to move toward the distal yoke portion 712 thereby decreasing the distance between the proximal yoke portion 716 and the distal yoke portion 712. Alternatively, rotation of the load adjustment member 714 relative to the proximal yoke portion 716 in a second direction opposite the first direction, for example a counterclockwise direction, may cause the proximal yoke portion 716 to move away from the distal yoke portion 712 thereby increasing the distance between the proximal yoke portion 716 and the distal yoke portion 712. Because the biasing member is stretched between the proximal yoke portion 716 and the distal yoke portion 712, increasing the distance between the proximal yoke portion 716 and the distal yoke portion 712 may increase the pre-load applied to the biasing member 704. On the other hand, decreasing the distance between the proximal yoke portion 716 and the distal yoke portion 712 may decrease the pre-load applied to the biasing member 704.

In certain instances, the pre-load applied against the biasing member 704 is set to a predetermined value during the assembly of the surgical instrument 10. To set the pre-load, the load adjustment member 714 can be turned clockwise and/or counterclockwise, for example, until the predetermined value of the pre-load load is realized by a load monitoring unit, for example. Once the pre-load is set to the predetermined value, the load adjustment assembly 710 can be assembled with the handle assembly 12.

In certain instances, the distance between the proximal yoke portion 716 and the distal yoke portion 712 can be fixed to maintain the pre-load at the predetermined value. In certain instances, the distance between the proximal yoke portion 716 and the distal yoke portion 712 can be fixed by fixing the load adjustment member 714 to proximal yoke portion 716. In at least one example, the load adjustment member 714 can be fixed to the proximal yoke portion 716 by welding the load adjustment member 714 to the proximal yoke portion 716. In at least one example, the load adjustment member 714 can be fixed to the proximal yoke portion 716 by gluing the load adjustment member 714 to the proximal yoke portion 716. Other techniques for fixing the load adjustment member 714 to the proximal yoke portion 716 are contemplated by the present disclosure.

Figure 29:
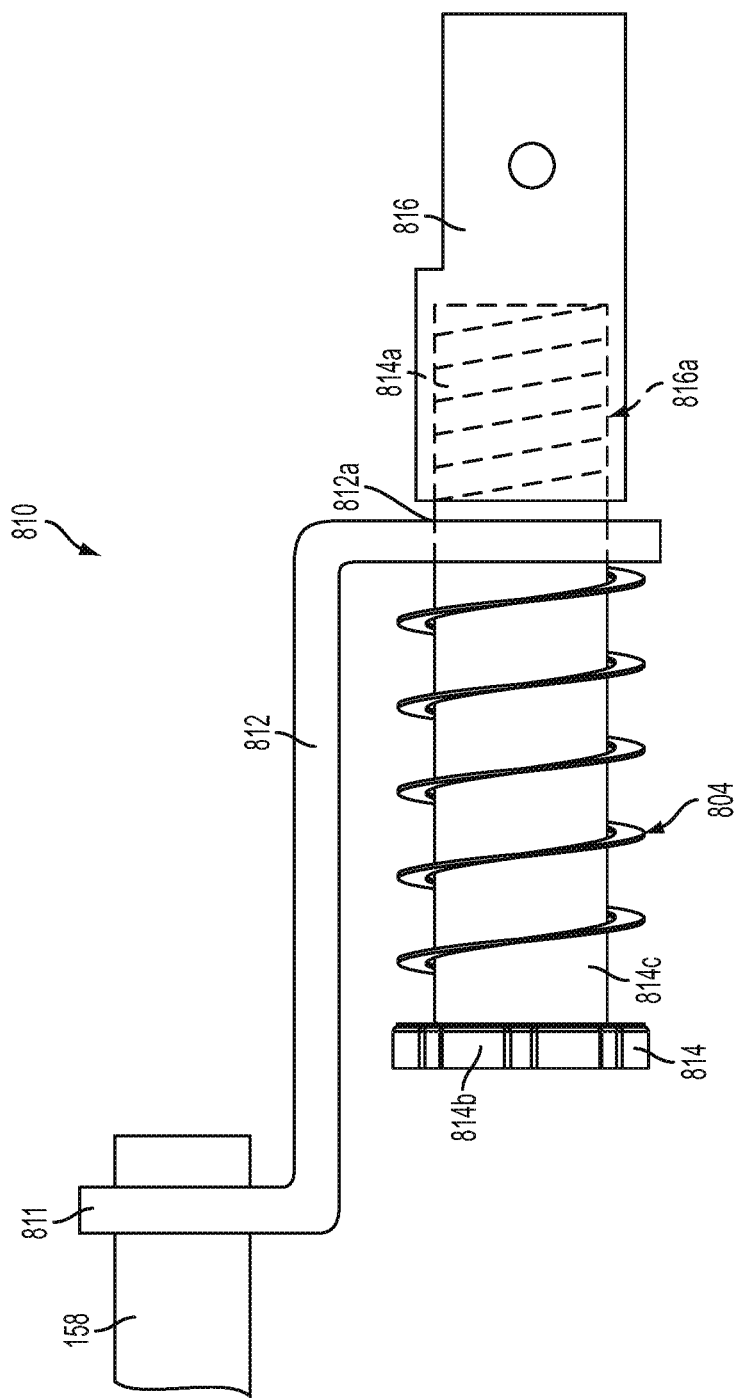
FIG. 29 illustrates a side-elevational view of a load adjustment assembly of the surgical instrument of FIG. 2.

Referring now to FIG. 29, in certain instances, the handle assembly 12 of the surgical instrument 10 may include a load adjustment assembly 810, which is similar in many respects to the load adjustment assembly 710. For example, like the load adjustment assembly 710, the load adjustment assembly 810 is operably coupled to a drive shaft of the surgical instrument 10 such as, for example, the outer tubular sheath 56 or the inner tubular member 158. Furthermore, like the load adjustment assembly 710, the load adjustment assembly 810 can be employed to adjust an initial load (a pre-load) applied against a biasing member 804. As described in greater detail below, the biasing member 804 can be configured to protect from transmission of excessive actuation forces greater than the pre-load to a clamp member of the surgical instrument 10.

As illustrated in FIG. 29, the load adjustment assembly 810 may include a distal yoke portion 812, a proximal yoke portion 816, and a load adjustment member 814. In certain instances, the load adjustment member 814 may comprise a threaded proximal portion 814a and a distal stop 814b. In certain instances, the biasing member 804 may comprise a compression spring which can be located at least partially around a body portion 814c of the load adjustment member 814. In such instances, the biasing member 804 can be compressed between the distal stop 814b and a coupling member 812a of the distal yoke portion 812.

In certain instances, as illustrated in FIG. 29, the coupling member 812a can be movably engaged with the load adjustment member 814. For example, the coupling member 812a may comprise a through-hole which can be configured to receive the body portion 814c of the load adjustment member 814. In certain instances, the coupling member 812a can be slidably moved relative to the body portion 814c of the load adjustment member 814, for example. In such instances, the biasing member 804 may cause the coupling member 812a of the distal yoke portion 812 to be abutted against the proximal yoke portion 816, as illustrated in FIG. 29.

Further to the above, referring again to FIG. 29, the threaded proximal portion 814a can be received, or at least partially received, within a receiving portion 816a of the proximal yoke portion 816. For example, the receiving portion 816a may include a thread on an internal wall of the receiving portion 816a which can be threadedly engaged with the threaded proximal portion 814a, for example.

Further to the above, the distal yoke portion 812 can be operably coupled to a drive shaft of the surgical instrument 10 such as, for example, the outer tubular sheath 56 or the inner tubular member 158. FIG. 29 shows a drive collar 811 coupling the distal yoke portion 812 to the inner tubular member 158. In addition, the proximal yoke portion 816 may be operably coupled to the trigger 32 of the handle assembly 12. For example, a linkage assembly may couple the trigger 32 to the proximal yoke portion 816. As described above, the trigger 32 can be pivotably moved relative to the fixed handle 34 to reciprocate the inner tubular member 158 axially between a first position and a second position; and the clamp member 164 can be transitioned between an open configuration and a closed configuration with respect the ultrasonic blade 66 in response to the reciprocating motion of the inner tubular member 158 between the first position and the second position.

In use, the trigger 32 can be pivoted toward the fixed handle 34 to apply a force to the load adjustment assembly 810 to transition the load adjustment assembly 810 and the inner tubular member 158 proximally thereby causing the clamp member 164 to be actuated toward the closed configuration, for example. The force applied to the clamp member 164 of the surgical instrument 10 by pivotal movement of the trigger 32 acting through the load adjustment assembly 810 can be limited, or at least partially limited, by the biasing member 804. In certain instances, as described above, the biasing member 804 may comprise a compression spring which can be compressed between the distal stop 814b and the coupling member 812a, abutted against the proximal yoke portion 816, to set a biasing member pre-load to a predetermined value. The pre-load can be adjusted to the predetermined value by employing the load adjustment member 714 to adjust the distance between the distal stop 814b and the coupling member 812a of the distal yoke portion 812, as described in greater detail below.

In certain instances, the biasing member 804 may limit force transmission from the trigger 32 to the clamp member 164 if excessive force is applied to the trigger 32 by a user of the surgical instrument 10. When the force, which is applied by the user to the trigger 32, is less than the pre-load limit of the biasing member 704, the load adjustment assembly 810 moves as a single unit to reciprocate the inner tubular member 158 and actuate the clamp member 164. In other words, a force less than the pre-load limit of the biasing member 804 does not result in relative motion between the distal stop 814b and the coupling member 812a. Said another way, if the force applied by the user through the trigger 32 is less than the pre-load limit of the biasing member 804, the coupling member 812a remains abutted against the proximal yoke portion 816 as the load adjustment assembly 810 moves to cause the inner tubular member 158 to actuate the clamp member 164 to the closed configuration.

However, when the force, which is applied by the user to the trigger 32, exceeds the pre-load limit of the biasing member 804, the biasing member 804 may be further compressed between the distal stop 814b and the coupling member 812a thereby causing the coupling member 812a to move away from the proximal yoke portion 816 for a limited degree thereby limiting the transmission of the excessive force to the inner tubular member 158 and the clamp member 164.

The load adjustment member 814 can be employed to compress the biasing member 804 between the distal stop 814b and the coupling member 812a to an initial compressed condition corresponding to a desired pre-load by adjusting the distance between the distal stop 814b and the proximal yoke portion 816 abutting against the coupling member 812a. For example, rotation of the load adjustment member 814 relative to the proximal yoke portion 816 in a first direction, for example a clockwise direction, may cause the proximal yoke portion 816 to move toward the distal yoke portion 812 thereby decreasing the distance between the distal stop 814b and the coupling member 812a. Alternatively, rotation of the load adjustment member 814 relative to the proximal yoke portion 816 in a second direction opposite the first direction, for example a counterclockwise direction, may cause the proximal yoke portion 816 to move away from the distal yoke portion 812 thereby increasing the distance between the distal stop 814b and the coupling member 812a. Because the biasing member is compressed between the distal stop 814b and the coupling member 812a, increasing the distance between the distal stop 814b and the coupling member 812a may decrease the pre-load applied to the biasing member 804. On the other hand, decreasing the distance between the distal stop 814b and the coupling member 812a may increase the pre-load applied to the biasing member 804.

In certain instances, the pre-load applied against the biasing member 804 is set to a predetermined value during the assembly of the surgical instrument 10. To set the pre-load, the load adjustment member 814 can be turned clockwise and/or counterclockwise, for example, until the predetermined value of the pre-load is realized by a load monitoring unit, for example. Once the pre-load is set to the predetermined value, the load adjustment assembly 810 can be assembled with the handle assembly 12.

In certain instances, the distance between the distal stop 814b and the coupling member 812a can be fixed to maintain the pre-load at the predetermined value. In certain instances, the distance between the distal stop 814b and the coupling member 812a can be fixed by fixing the load adjustment member 814 to proximal yoke portion 816. In at least one example, the load adjustment member 814 can be fixed to the proximal yoke portion 816 by welding the load adjustment member 814 to the proximal yoke portion 816. In at least one example, the load adjustment member 814 can be fixed to the proximal yoke portion 816 by gluing the load adjustment member 814 to the proximal yoke portion 816. Other techniques for fixing the load adjustment member 814 to the proximal yoke portion 816 are contemplated by the present disclosure.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument for use in a surgical procedure, comprising:
   an ultrasonic transducer;
   an ultrasonic blade, wherein the ultrasonic blade is acoustically coupled to the ultrasonic transducer;
   a clamp member pivotably movable between an open configuration and an approximated configuration relative to the ultrasonic blade;
   a reciprocating actuation member operably coupled to the clamp member, wherein the reciprocating actuation member is actuatable between a first position and a second position, and wherein the clamp member moves between the open configuration and the approximated configuration in response to movement of the reciprocating actuation member between the first position and the second position;
   a load adjustment assembly that applies an initial load against the reciprocating actuation member, wherein the initial load is maintained by the load adjustment assembly at a predetermined value during the surgical procedure,
   wherein the load adjustment assembly comprises:
      a stop;
      a load adjustment member; and
      a biasing member extending between the stop and the load adjustment member,
      wherein the initial load is adjustable to the predetermined value by adjusting a distance between the stop and the load adjustment member.

2. The ultrasonic surgical instrument of claim 1, further comprising a drive shaft extending from the reciprocating actuation member to the clamp member, wherein the drive shaft transmits movement of the reciprocating actuation member between the first position and the second position to the clamp member.

3. The ultrasonic surgical instrument of claim 2, wherein the drive shaft extends through the reciprocating actuation member and the load adjustment assembly.

4. The ultrasonic surgical instrument of claim 1, further comprising:
   a drive shaft, wherein
   the stop is coupled to the drive shaft,
   the load adjustment member is attachable to the drive shaft at a proximal location to the stop, and
   the biasing member extends between the stop and the load adjustment member, and is configured to apply the initial load against the reciprocating actuation member.

5. The ultrasonic surgical instrument of claim 4, wherein the load adjustment member is fixedly attached to the drive shaft at a final distance between the stop and the load adjustment member, wherein the final distance corresponds to the predetermined value of the initial load.

6. The ultrasonic surgical instrument of claim 1, further comprising:
   a drive shaft, wherein the load adjustment assembly further comprises:
a collar at least partially disposed around the drive shaft, wherein
the collar comprises the stop at a distal end of the collar,
the load adjustment member is located at a proximal location to the stop, and
the biasing member extends between the stop and the load adjustment member and is configured to apply the initial load against the reciprocating actuation member.

7. The ultrasonic surgical instrument of claim 6, wherein the collar comprises a threaded proximal portion, wherein the load adjustment member is threadedly engaged with the threaded proximal portion.

8. An ultrasonic surgical instrument for use in a surgical procedure, comprising:
an ultrasonic transducer;
an ultrasonic blade, wherein the ultrasonic blade is acoustically coupled to the ultrasonic transducer;
a clamp member pivotably movable between an open configuration and an approximated configuration relative to the ultrasonic blade;
a reciprocating actuation member operably coupled to the clamp member, wherein the reciprocating actuation member is actuatable between a first position and a second position, and wherein the clamp member moves between the open configuration and the approximated configuration in response to movement of the reciprocating actuation member between the first position and the second position;
a load adjustment assembly that applies an initial load against the reciprocating actuation member, wherein the initial load is maintained by the load adjustment assembly at a predetermined value during the surgical procedure; and
a drive shaft extending from the reciprocating actuation member to the clamp member, wherein the drive shaft transmits movement of the reciprocating actuation member between the first position and the second position to the clamp member,
wherein the load adjustment assembly comprises:
a stop coupled to the drive shaft;
a load adjustment member attachable to the drive shaft at a proximal location to the stop; and
a biasing member extending between the stop and the load adjustment member, wherein the biasing member is configured to apply the initial load against the reciprocating actuation member, wherein the initial load is adjustable to the predetermined value by adjusting a distance between the stop and the load adjustment member.

9. An ultrasonic surgical instrument for use in a surgical procedure, comprising:
an ultrasonic transducer;
an ultrasonic blade, wherein the ultrasonic blade is acoustically coupled to the ultrasonic transducer;
a clamp member pivotably movable between an open configuration and an approximated configuration relative to the ultrasonic blade;
a reciprocating actuation member operably coupled to the clamp member, wherein the reciprocating actuation member is actuatable between a first position and a second position, and wherein the clamp member moves between the open configuration and the approximated configuration in response to movement of the reciprocating actuation member between the first position and the second position;
a load adjustment assembly that applies an initial load against the reciprocating actuation member, wherein the initial load is maintained by the load adjustment assembly at a predetermined value during the surgical procedure; and
a drive shaft extending from the reciprocating actuation member to the clamp member, wherein the drive shaft transmits movement of the reciprocating actuation member between the first position and the second position to the clamp member,
wherein the load adjustment assembly further comprises:
a collar at least partially disposed around the drive shaft, wherein the collar comprises a stop at a distal end of the collar;
a load adjustment member located at a proximal location to the stop; and
a biasing member extending between the stop and the load adjustment member, wherein the biasing member is configured to apply the initial load against the reciprocating actuation member, wherein the initial load is adjustable to the predetermined value by adjusting a distance between the stop and the load adjustment member.

* * * * *